(12) United States Patent
Jaeger

(10) Patent No.: US 11,612,514 B2
(45) Date of Patent: Mar. 28, 2023

(54) METHODS AND DEVICES FOR THERMOREGULATION OF CORE BODY TEMPERATURE THROUGH APPLICATION OF NEAR INFRARED RADIATION AND LOCALIZED THERMAL TRANSFER ON SKIN SURFACES

(71) Applicant: Eric Matthew Jaeger, Southlake, TX (US)

(72) Inventor: Eric Matthew Jaeger, Southlake, TX (US)

( * ) Notice: Subject to any disclaimer, the term of this patent is extended or adjusted under 35 U.S.C. 154(b) by 590 days.

(21) Appl. No.: 16/807,579

(22) Filed: Mar. 3, 2020

(65) Prior Publication Data

US 2021/0275349 A1  Sep. 9, 2021

(51) Int. Cl.
*A61F 7/02* (2006.01)
*A61F 7/00* (2006.01)

(52) U.S. Cl.
CPC ........ *A61F 7/02* (2013.01); *A61F 2007/0036* (2013.01); *A61F 2007/0047* (2013.01); *A61F 2007/0056* (2013.01); *A61F 2007/0088* (2013.01); *A61F 2007/0225* (2013.01)

(58) Field of Classification Search
CPC .............................. A61N 5/0625; A61F 7/007
See application file for complete search history.

(56) References Cited

U.S. PATENT DOCUMENTS

| 5,683,438 A | 11/1997 | Grahn |
| 6,572,638 B1 | 6/2003 | Dae et al. |
| 6,656,208 B2 | 12/2003 | Grahn et al. |
| 8,066,752 B2 | 11/2011 | Hamilton et al. |
| 8,177,826 B2 | 5/2012 | Grahn et al. |
| 2003/0040783 A1* | 2/2003 | Salmon ................ A61N 5/0625 607/108 |

(Continued)

FOREIGN PATENT DOCUMENTS

JP  2001327614 A  11/2001

OTHER PUBLICATIONS

Smith, K. C. (ed), The Science of Photobiology, 1st edition, 1977, Chapter 15, pp. 397-417.

(Continued)

*Primary Examiner* — Kaitlyn E Smith
(74) *Attorney, Agent, or Firm* — Mauriel Kapouytian Woods LLP; Benjamin Charkow

(57) ABSTRACT

The invention presents methods and devices for controlling and modifying the core body temperature of a human or other mammal. The apparatus contains an element to be placed in contact with an individual's skin, such as the palm of a hand or sole of a foot; the element emits radiation, preferably within the red to infrared range of 550 nm to 950 nm, inducing vasodilation and increased blood flow in the region beneath the contacting area. A heat exchange element is concurrently in contact with the skin, capable of transferring heat into or removing heat from the circulatory vasculature, through the skin surface. The circulatory system carries the increase or decrease in thermal energy to the body's core organs. As such the method and devices are capable of increasing or decreasing the core body temperature, or maintaining current core body temperature in the presence of external thermal elements.

11 Claims, 29 Drawing Sheets

(56) References Cited

U.S. PATENT DOCUMENTS

| | | | | |
|---|---|---|---|---|
| 2006/0235494 | A1* | 10/2006 | Vanderschuit | A61F 7/02 607/89 |
| 2012/0004711 | A1* | 1/2012 | Hilty | A61N 5/062 607/90 |
| 2015/0165231 | A1* | 6/2015 | Scheja | A61N 5/062 604/20 |
| 2016/0367833 | A1 | 12/2016 | Salinas et al. | |
| 2017/0281435 | A1 | 10/2017 | Diller et al. | |

OTHER PUBLICATIONS

Mahmood, U. et al., "Near-Infrared Optical Imaging of Proteases in Cancer," Molecular Cancer Therapeutics, vol. 2, 489-496, May 2003.

Daniel Gagnon et al., "Cold-Water Immersion and the Treatment of Hyperthermia: Using 38.66C as a Safe Rectal Temperature Cooling Limit," Journal of Athletic Training 2010;45(5):439-44.

Cory L. Butts, MS et al., "Physiologic and Perceptual Responses to Cold Shower Cooling After Exercise-Induced Hyperthermia," Journal of Athletic Training 2016;51(3):252-257.

Drs. H.A.M. Daanen, Arterio-venous Anastomoses and Thermoregulation, Report No. IZF 1991 B-12, TNO Defence Research.

Richard E. Klabunde, Ph.D, "Cardiovascular Physiological Concepts textbook," published Sep. 2011.

Eleanor R. Adair et al., "Thermoregulatory Responses to RF Energy Absorption, Bioelectromagnetics Supplement," 6:S17-S38(2003).

Nicole L. Lohr et al., "Enhancement of nitric oxide release from nitrosyl hemoglobin and nitrosyl myoglobin by red/near infrared radiation: Potential role in cardioprotection," Journal of Molecular and Cellular Cardiology, vol. 47, Issue 2, Aug. 2009, pp. 256-263.

Michael C.H. Mak et al., "Immediate Effects of Monochromatic Infrared Energy on Microcirculation in Healthy Subjects," Photomedicine and Laser Surgery, vol. 30, No. 4, 2012.

Kelly K. Good et al., "Postoperative hypothermia—The chilling consequences," AORN Journal, May 2006, vol. 83, No. 5.

Nisha Charkoudian, Ph.D, "Skin Blood Flow in Adult Human Thermoregulation: How It Works, When It Does Not, and Why," Mayo Clinic Proceedings Journal, May 2003, vol. 7.

Harry T. Whelan, M.D. et al., "Effect of NASA Light-Emitting Diode Irradiation on Wound Healing," Journal of Clinical Laser Medicine & Surgery, vol. 19, No. 6, 2001.

International Searching Authority (ISA), Notification of Transmittal of the International Search Report and the Written Opinion of the International Searching Authority, for International Application No. PCT/US21/19187, 9 pp., dated May 11, 2021.

* cited by examiner

METHODS AND DEVICES FOR THERMOREGULATION OF CORE BODY TEMPERATURE THROUGH APPLICATION OF NEAR INFRARED RADIATION AND LOCALIZED THERMAL TRANSFER ON SKIN SURFACES

FIELD OF THE INVENTION

The present invention generally relates to methods and devices for thermoregulation of a living body and more particularly through direct skin contact with a heat transfer mechanism. The methods and devices of the invention may be applied to both humans and animals.

BACKGROUND OF THE INVENTION

The human body possesses complex mechanisms for regulating its core body temperature—the temperature of vital organs such as the heart, lungs, liver, and kidneys. This process is known as thermoregulation. Thermoregulation is vital to the well-being and survival of humans and other mammalian animals. Commonly known human thermoregulatory mechanisms include shivering during hypothermia and sweating during hyperthermia.

Hyperthermia, defined as a state of above normal core body temperature, has been treated through many different modalities. Cooling vests, cooling blankets, cold water baths, ice packs and misting systems are some of the many devices intended to cool the body down through typical conductive heat transfer at the skin surface. These devices do not attempt to override or manipulate the typical human thermoregulatory response to skin contact with cold entities. Some of them may trigger the oppositely desired effect—skin contact with a cold surface can results in locally reduced skin blood flow, reducing the rate of heat exchange and exasperating the cooling mechanism. Other modalities, while effectively lowering skin temperature, are bulky, non-portable, require high energy input, and require a significant amount of time to cool the core temperature of the body. Only full body cold water immersion has been shown to rapidly cool the core temperature of the body.

Hypothermia, defined as a subnormal core body temperature, has been treated with devices utilizing similar skin conductive heat transfer, such as heating blankets, heated clothing and heat exchange blankets. These devices can be bulky, heavy, and require high energy input. A typical physiological response to hypothermia is a reduction in skin blood flow, reducing the rate of heat transfer to the body's core.

Thermal homeostasis for humans can be defined as a core body temperature in the range of 35.0 to 37.5° C. A core temperature in this range is referred to as being normothermic.

Invasive treatments designed to modify core body temperature, e.g., to maintain thermal homeostasis, may involve intravenous injection of cool or warm fluids such as saline solution, external blood heat exchangers, and injection of intravenous pharmacological thermoregulatory inhibitors. See U.S. Pat. No. 6,572,638B, to Dae et al. These treatments are generally effective in rapidly cooling or warming core body temperature, and have been successfully used to return a person's core body temperature to its normothermic range. They can also be utilized to induce hypothermia for neuroprotection during surgical procedures, such as coronary artery bypass, cerebral aneurysm repair, brain injury trauma and post cardiac arrest. However, invasive treatments require sophisticated equipment and expertise, require a hospital location, result in high expense, and expose the patient to serious medical risks such as infection and bleeding.

The primary non-invasive thermoregulatory mechanism for humans is an increase or decrease of blood flow to the skin, which directly regulates heat exchange between the vasculature and the external environment. Skin blood flow is approximately 250 ml/min when core body temperature falls within the normothermic range. Skin blood flow can increase to 8,000 ml/min during extreme hyperthermia and can decrease to 25 ml/min during hypothermia or exposure to cold environments or cold surfaces.

Methods and devices that utilize negative pressure on a hand or foot to induce localized vasodilation, combined with concurrent heating or cooling, have been described and patented. See U.S. Pat. No. 5,683,438, to Dennis A Grahn, U.S. Pat. No. 8,177,826 to Grahn et al, U.S. Pat. No. 6,656,208 to Grahn et al, U.S. Pat. No. 8,066,752, Hamilton et al. Published results have shown these to be effective in cooling or warming core body temperature, presumably overriding the thermoregulatory mechanism of the body to open arteriovenous anastomoses ("AVA"), which are low-resistance blood vessels that allow high flow rates directly from arterioles to venules, bypassing capillaries. However, these devices require cumbersome and bulky enclosures that must form an airtight seal around a person's extremities, while drawing a vacuum on the extremity, and maintaining intimate contact with a heat exchange device inside the enclosure. These systems are inherently bulky, require costly vacuum pumping systems and sealing systems in addition to heat exchange systems, do not function well for immobilized or non-lucid individuals, and may have restrictive portability.

While heat exchange can take place at any skin surface, glabrous skin areas are specific regions of the body in which heat exchange is greatly maximized. On humans these regions include but are not limited to the palms of the hands and soles of the feet. AVAs are located directly beneath glabrous skin locations. The AVAs can be opened or closed in response to the body's thermoregulatory mechanisms, causing substantial changes in skin blood flow. It is these regions where heat exchange with the environment has the greatest effect on core body temperature.

One of ordinary skill in the art will recognize that core body temperature can be manipulated and controlled through the addition or removal of thermal energy at these glabrous skin locations. However, the inherent mammalian thermoregulatory response during these efforts often results in closure of the AVAs, reducing or preventing heat exchange from taking place. For example, a typical remedy for a person experiencing hyperthermia is to apply a cold object to the surface of the skin. However, the intrinsic thermoregulatory response to a cold object placed against the skin results in localized vasoconstriction, the narrowing and or closing of local blood vessels, resulting in significantly reduced local skin blood flow. This greatly reduces the ability to remove heat from the circulatory system, and by extension, reduces the ability to reduce core body temperature.

Additionally, certain disease states and pharmacological side effects result in loss of suitable thermoregulatory control. Thus, there is a need to develop methods and devices in which the local thermoregulatory mechanism is manipulated and/or overridden, such that AVAs are forced to remain open. When forced open, a high rate of heat exchange can then occur in the AVAs at these manipulated skin locations, rapidly heating, cooling, or maintaining the core body temperature.

SUMMARY OF THE INVENTION

The invention as disclosed presents non-invasive methods and devices for controlling and modifying an individual's core body temperature.

The invention provides for transferring heat into or removing heat from the circulatory vasculature, through the skin surface. The invention also provides for overriding the intrinsic human and mammalian thermoregulatory responses to external thermal elements that lead to a reduction in thermal transfer across the skin.

The invention as disclosed provides for transferring heat energy into or removing heat from the circulatory vasculature through direct skin contact with a heat transfer mechanism, such as, in exemplary embodiments, circulating fluid or a thermoelectric heat pump (Peltier device). Heat is transferred into or removed from the vascular system directly beneath the location of skin contact. In embodiments, the surface of the heat pump is within the range of 1° C. to 50° C. and the circulating fluid can similarly range from 1° C. to 50° C. The human circulatory system then carries the increase or decrease in thermal energy to the body's core organs. The location of skin contact is bathed in electromagnetic radiation within the range of 550 nm to 950 nm through the use of radiation emitting devices that operate in the red and near infrared frequency.

Heretofore, infrared electromagnetic radiation devices have been developed and commercialized for use in enhanced plant growth, and for treating humans in the areas of improved wound healing, pain reduction and chronic and acute injury recovery. These devices have been developed as multi-chromatic and monochromatic devices, utilizing laser and light emitting diode energy sources. Commercial success has been found with monochromatic infrared energy (MIRE) devices utilizing a light emitting diode (LED) array energy source, such as devices supplied by Anodyne Systems and Quantum Devices.

In accordance with the present invention, it has been discovered that through a complex photo-biochemical response, exposing skin to this electromagnetic radiation creates sustained vasodilation and increased blood flow in the region beneath the skin contacting area, overriding the body's thermoregulatory response to the temperature at the location of skin contact, and regardless of the external environmental factors such as heat, cold or humidity. Physiological testing, described herein, has shown that exposing the palm of a hand, located directly above arteriovenous anastomoses (AVA) vasculature, to monochromatic electromagnetic radiation within the range of 550 nm to 950 nm, creates vasodilation and increased blood flow in the AVA vasculature, despite the presence of ice surrounding the hand and cold water circulating on the skin of the palm, which in itself causes vasoconstriction. The testing also demonstrated that heat was removed from the body while in the presence of the applied monochromatic electromagnetic radiation, and that heat was not removed when the monochromatic electromagnetic radiation was not applied. Following is a description of the photo-biochemical response mechanism, initiated by exposure to electromagnetic radiation, which results in a localized increase in blood flow.

1. Skin tissue with substantial local vasculature is exposed to electromagnetic radiation, emitted from MIRE in the near-infrared to infrared spectrum, preferably within the wavelength range of 550 nm to 950 nm. In embodiments, a peak wavelength is chosen, preferably within the range of 670 nm to 890 nm. The radiation can be delivered via laser or LED. Typical methods include MIRE emitted via a LED array.

2. Skin, tissue and water have minimal absorption of MIRE in the range stated above. Therefore the MIRE readily penetrates across the skin and into the body. Hemoglobin proteins, located within red blood cells in the blood vessels beneath the skin, maximally absorb the MIRE that has penetrated into the body.

3. Hemoglobin protein is known to store significant amounts of nitric oxide.

4. When exposed to MIRE, hemoglobin proteins release nitric oxide into the blood stream.

5. The nitric oxide diffuses into the smooth muscle cells of the surrounding vasculature, where it binds to and activates the enzyme guanylyl cyclase.

6. Guanylyl cyclase catalyzes the conversion of GTP (Guanosine triphosphate) to cGMP (cyclic guanosine monophosphate) within the smooth muscle cells of the surrounding vasculature.

7. cGMP induces smooth muscle relaxation through multiple mechanisms, most notably through relaxation of contractile proteins located within the smooth muscle cells.

8. Smooth muscle relaxation within the vasculature results in vasodilation of the local blood vessels.

9. Vasodilation of the local blood vessels directly causes an increase in local blood flow, in this case, near to the surface of the skin.

Nitric oxide has been documented to be a powerful vasodilator, with the presence of only small amounts required to cause a significant increase in blood flow. It is well known to one of ordinary skill in the art that an elevated level of skin blood flow is essential to sustaining a high rate of heat transfer across the skin surface. Studies have shown that just an 8% increase in skin blood flow rate, compared to normal, can result in up to a doubling of the heat transfer rate across the skin.

In an embodiment where the method is practiced or the device is applied at a location of glabrous skin, the rate of thermal energy transfer will be significantly increased, with the selective infrared radiation overriding the local thermoregulatory response and the AVA vasculature remaining open, resulting in rapid heating or cooling of core body temperature, or the maintenance of normothermic temperature during exposure to adverse environmental factors or extreme exertion. However, it is understood that in embodiments, the invention can be practiced at any suitable open skin area.

According to an exemplary embodiment of the present invention there is provided a device for modifying mammalian core temperature, comprising a first infrared energy source capable of emitting a first monochromatic infrared radiation with a central wavelength between 550 to 950 nm, a first translucent fluid bladder for thermal transfer, a first translucent substrate with a first surface in contact with the first translucent fluid bladder and a second surface configured to be in contact with a first open skin area of a mammal with a core temperature, a first fluid perfusion unit capable of circulating a first fluid through the first translucent fluid bladder and the first fluid set at a temperature above or below the core temperature of the mammal. In this exemplary embodiment, the first monochromatic infrared radiation from the first infrared energy source is capable of being directed through the first translucent fluid bladder and the first translucent substrate. In embodiments, the first translucent substrate is integral to the first translucent fluid bladder. In embodiments, the device is configured to fit in a human hand and cover either the palm of the human hand or the palm of the human hand and the finger surfaces of the hand.

In another exemplary embodiment, the device is structured to modify the mammalian core temperature via heat transfer across two outer skin surfaces, such as the palm of two hands. In this exemplary embodiment, the device further comprises a second infrared energy source capable of emitting a second monochromatic infrared radiation with a central wavelength between 550 to 950 nm, second translucent fluid bladder for thermal transfer, a second translucent substrate with a third surface in contact with the second translucent thermal fluid bladder and a fourth surface configured to be in contact with a second open skin area of the mammal with the core temperature, a second fluid perfusion unit capable of circulating a second fluid through the second translucent fluid bladder, and the second fluid set at a temperature above or below the core temperature of the mammal. In this exemplary embodiment, the second monochromatic infrared radiation from the second infrared energy source is capable of being directed through the second translucent fluid bladder and the second translucent substrate.

According to an exemplary method carried out in accordance with the invention, a method for regulating a core body temperature of a mammal through addition or removal of thermal energy comprises monitoring the core body temperature of the mammal, placing an open skin area of the mammal in contact with a first surface of a first translucent substrate, directing a first infrared energy source emitting monochromatic infrared radiation energy with a central wavelength between 550 to 950 nm through a first translucent thermal transfer fluid bladder in contact with a second surface of the first translucent substrate and into the open skin area of the mammal, and circulating a first fluid, set at a temperature above or below the monitored core body temperature of the mammal, through a first fluid perfusion unit to raise or lower the core temperature of the mammal. One of ordinary skill in the art would understand that "monitoring" could be interpreted as a first responder or anyone noting an elevated or lowered core temp based on physiological signs and is different from 'measuring', which would require some sort of thermometer. In a preferred embodiment, monitoring is performed with or without a thermometer. In an embodiment, the open skin area in contact with a first surface of a first translucent substrate is a site where the AVA blood vessels are beneath the surface of the skin.

According to an exemplary method carried out in accordance with the invention, a method for regulating a core body temperature of a mammal through addition or removal of thermal energy comprises monitoring the core body temperature of the mammal, placing an open skin area of the mammal in contact with a first surface of a first translucent substrate, directing a first infrared energy source emitting monochromatic infrared radiation energy with a central wavelength between 550 to 950 nm through a second surface of the first translucent substrate and into the open skin area of the mammal and setting the temperature of a heat pump located in contact with a second surface of the first translucent substrate at a temperature above or below the monitored core body temperature of the mammal, to raise or lower the core temperature of the mammal.

In embodiments wherein heat energy is exclusively transferred into the body of the mammal, raising core temperature, the thermal energy transfer can be supplied via resistive electrical elements or electromagnetic radiation emission.

BRIEF DESCRIPTION OF THE DRAWINGS

Exemplary embodiments of this invention will be described with reference to the accompanying figures wherein:

FIG. 14b illustrates a schematic view along the vertical axis of the alternative embodiment shown in FIG. 14a.

DETAILED DESCRIPTION OF THE EXEMPLARY EMBODIMENTS

Figure 1:
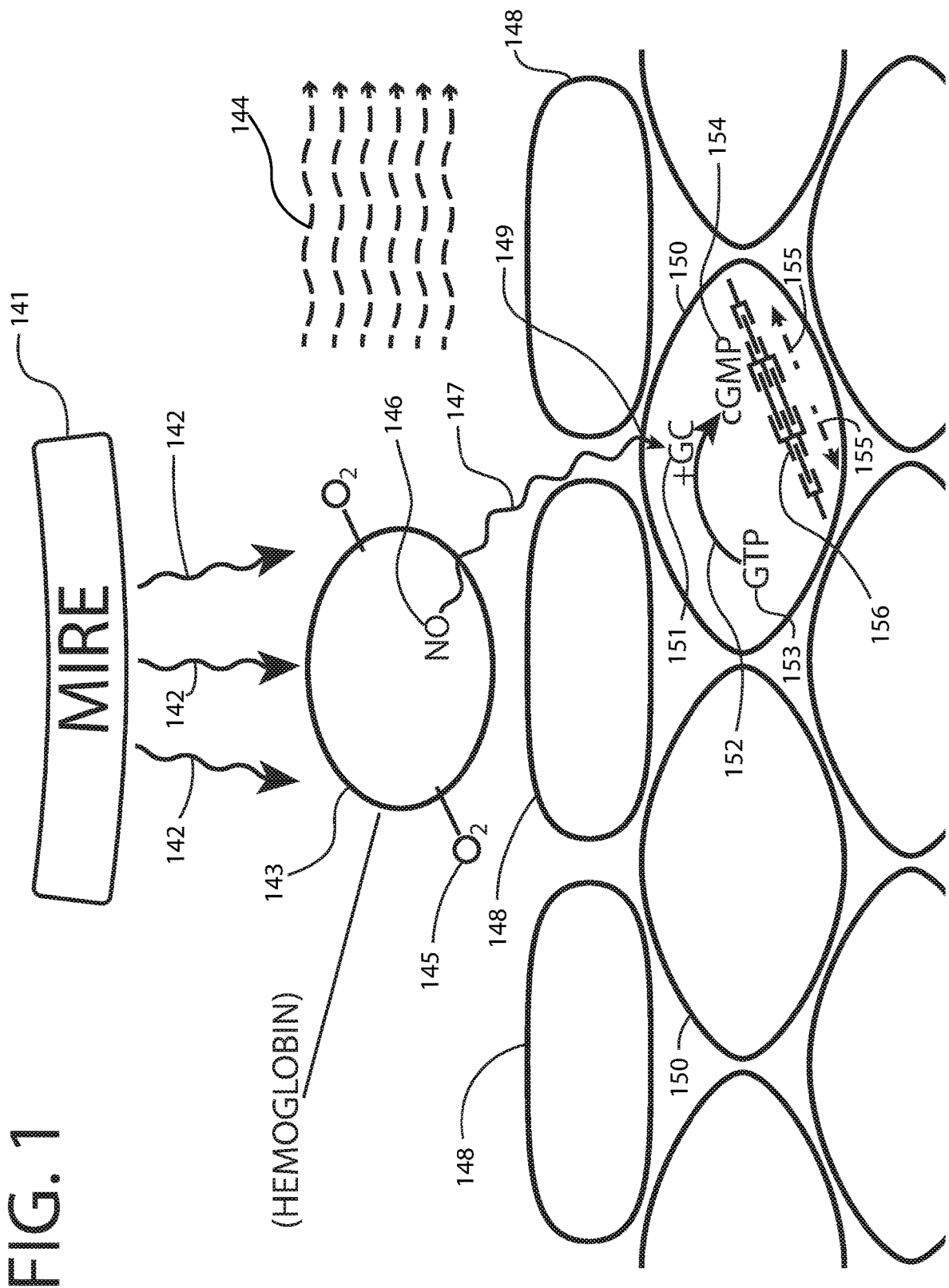
FIG. 1 illustrates the photo-biochemical mechanism for localized increase in skin blood flow.

Initially referring FIG. 1, the precise photo-biochemical mechanism for localized increase in skin blood flow through the use of the invention is described. FIG. 1 illustrates a schematic diagram of the causal reaction that begins with emitted infrared radiation 142 and results in cellular relaxation 155 of a smooth muscle cell 150 located within the inner lining an arteriovenous anastomoses blood vessel. Flow of blood 144 within the blood vessel is directionally tangential to endothelial cells 148 which line the inner surface of the blood vessel. Specifically, a MIRE light source 141 emits infrared radiation 142, which penetrates across the surface of the skin (not shown), through human tissues (not shown) and into the stream of blood flowing through the arteriovenous anastomoses blood vessel. Such infrared radiation 142 is readily absorbed by a hemoglobin protein 143, which is typically located within a red blood cell (not shown).

Absorption of this infrared radiation 142 causes a nitric oxide molecule 146 to be released 147 from the hemoglobin protein 143, into the stream of blood within the arteriovenous anastomoses blood vessel. The nitric oxide molecule passes beyond the endothelial cell 148 layer of the blood vessel inner lining and diffuses 149 into the smooth muscle cell 150, where it binds to and activates the guanylyl cyclase enzyme 151. Activated guanylyl cyclase enzyme 151 then catalyzes the conversion 152 of guanosine triphosphate 153 into cyclic guanosine monophosphate 154 within the smooth muscle cell 150. Cyclic guanosine monophosphate 154 induces smooth muscle relaxation through multiple mechanisms, most notably through relaxation 155 of contractile proteins 156 located within the smooth muscle cell 150. Multiple smooth muscle relaxation events cause vasodilation of the arteriovenous anastomoses blood vessel, which results in a sustained increase of localized blood flow. The sustained increase in blood flow allows for rapid heat exchange between the subject device and the human cardiovascular system, allowing for the regulating of the core temperature of the person in contact with the subject device.

Figure 2:
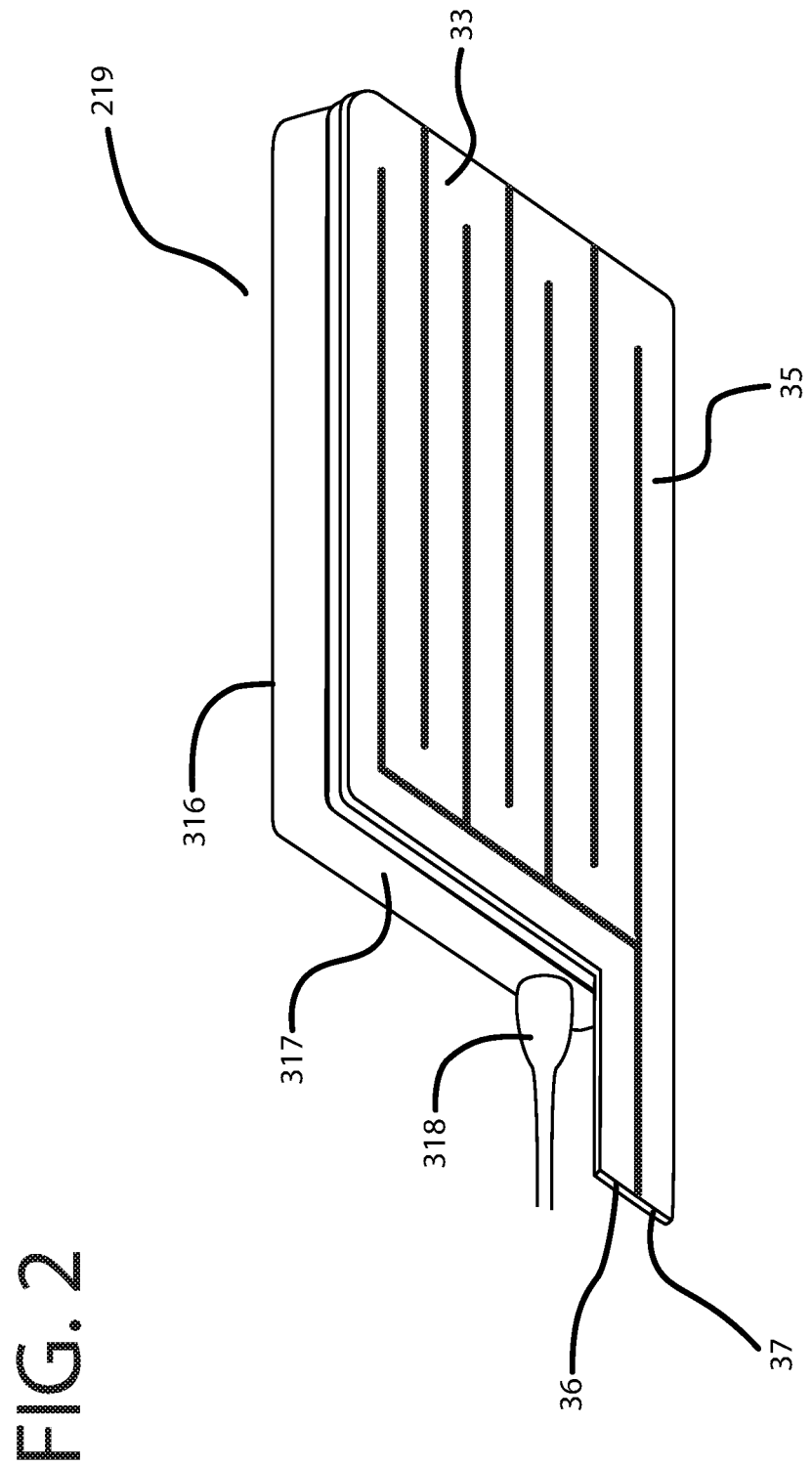
FIG. 2 illustrates a preferred embodiment of the claimed invention.
Figure 3:
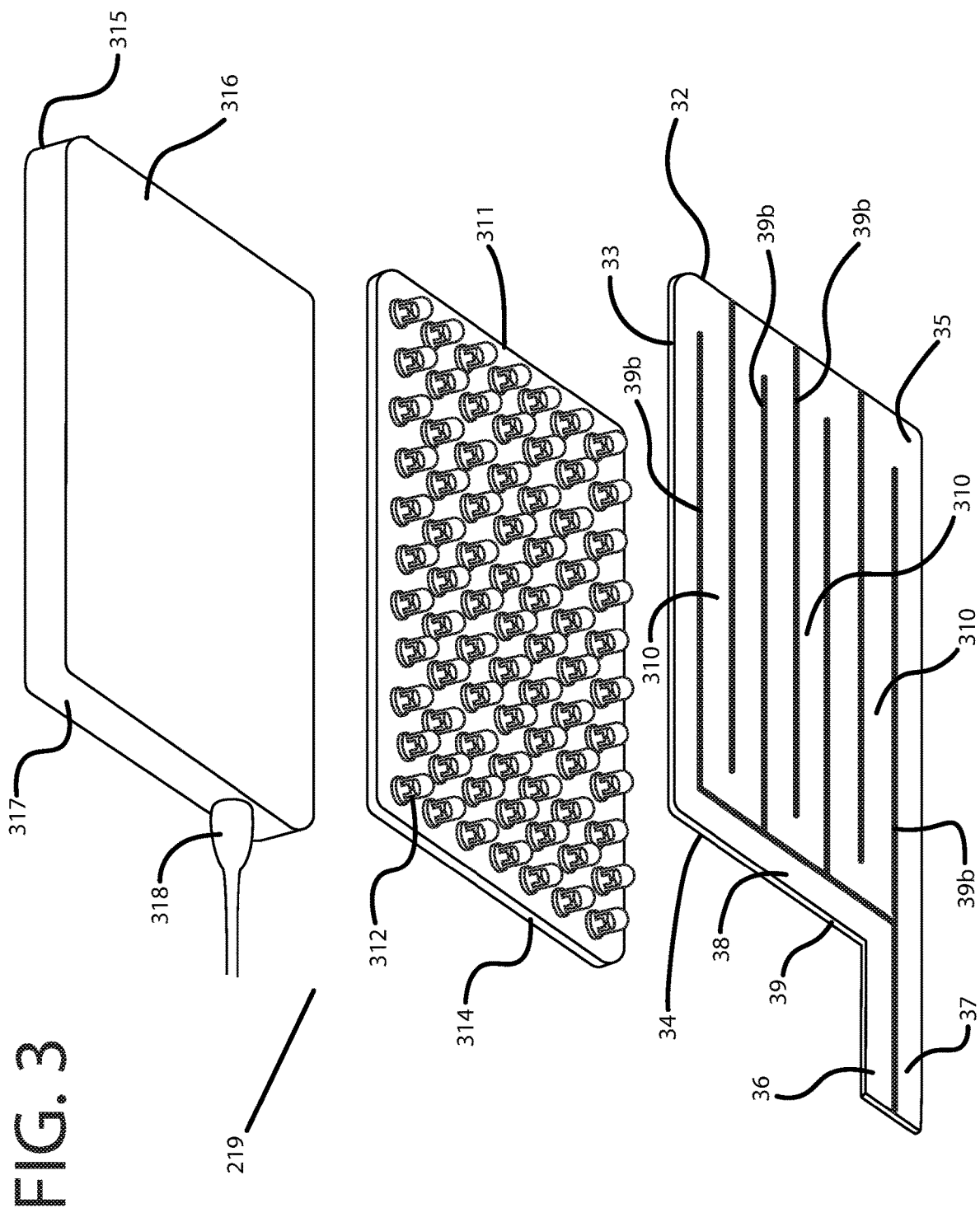
FIG. 3 is an exploded view of a preferred embodiment of the claimed invention.

FIG. 3 illustrates an exploded view of a near infrared thermal exchange module 219, with FIG. 2 showing an assembled view of the same.

In embodiments (not shown), the near infrared thermal exchange module 219 includes a fluid perfusion unit and a thermal control unit. Such units may be adapted to provide a stream of media such as water at elevated temperatures, lowered temperatures, or both, to module 219. Any sort of fluid perfusion and thermal conditioning unit combination may be used with the module 219 as would be apparent to one skilled in the art. Such a system would provide elevated temperatures when raising the core body temperature is desired, lowered temperatures when cooling the core body temperature is desired, or a set temperature of approximately 37° C. when homeostasis is desired.

As shown in FIG. 3, module 219 includes a translucent thermal transfer fluid bladder 33 which constitutes the bottom most portion 32 of module 219. Fluid bladder 33 may be made of polyvinyl chloride, polyurethane, polytetrafluoroethylene, or any compound that provides suitable transmittance of near infrared light, and which can be adapted to contain a water tight seal 39 along the periphery between the top surface 34 and a bottom, skin contacting surface 35. Fluid bladder 33 also contains a fluid inflow portion 36, connected to the fluid perfusion unit (not shown) and fluid outflow portion 37, also connected to the fluid perfusion unit. The fluid entering through the inflow portion 36 follows a fluid path 38 and enters into long fluid channels 310, which are defined by long sealed portions 39b, before exiting bladder 33 through the fluid outflow portion 37.

The central portion 311 of near infrared thermal exchange module 219 contains multiple near infrared light source devices 312, fixed to a mounting panel 314, which contains required electrical circuitry (not shown). In the preferred embodiment, light source devices 312 consist of near infrared light emitting diodes, although other methods may be used. Electronic circuitry may consist of any configuration that would be apparent to one of ordinary skill in the art.

Upper most portion 315 of module 219 consists of an outer casing 316 preferably made of plastic or metal, a housing module 317 which may contain additional electronic circuitry (not shown) required to control and provide power to the infrared light source devices 312, and a current carrying electrical cable 318 connected to an external power source (not shown), which may consist of common alternating current or battery supplied direct current, with or without power conditioning suitable for light source devices 312, which would be apparent to one of ordinary skilled in the art.

Figure 4:
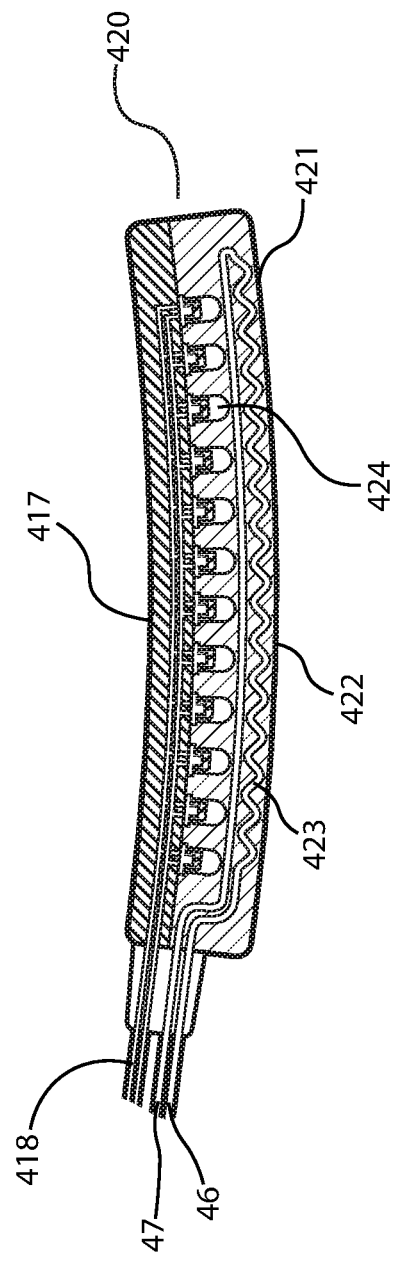
FIG. 4 illustrates a schematic cross-sectional view of an exemplary embodiment of the claimed invention.

FIG. 4 illustrates a schematic cross-sectional view 420 of an exemplary embodiment of the near infrared thermal exchange module 219 shown in FIG. 2. In this exemplary embodiment, the near infrared thermal exchange module has a curved surface 421 on the exterior bottom side 422 of the module. Bottom side 422 represents the skin contacting surface of the module, which is the bottom surface of the translucent thermal transfer fluid bladder 423. Multiple near infrared light emitting diodes 424 are mounted to housing module 417, and connected to an external power source (not shown) via current carrying electrical cable 418. Fluid bladder 423 contains a fluid inflow portion 46, connected to the fluid perfusion unit (not shown) and fluid outflow portion 47, also connected to the fluid perfusion unit.

Figure 5:
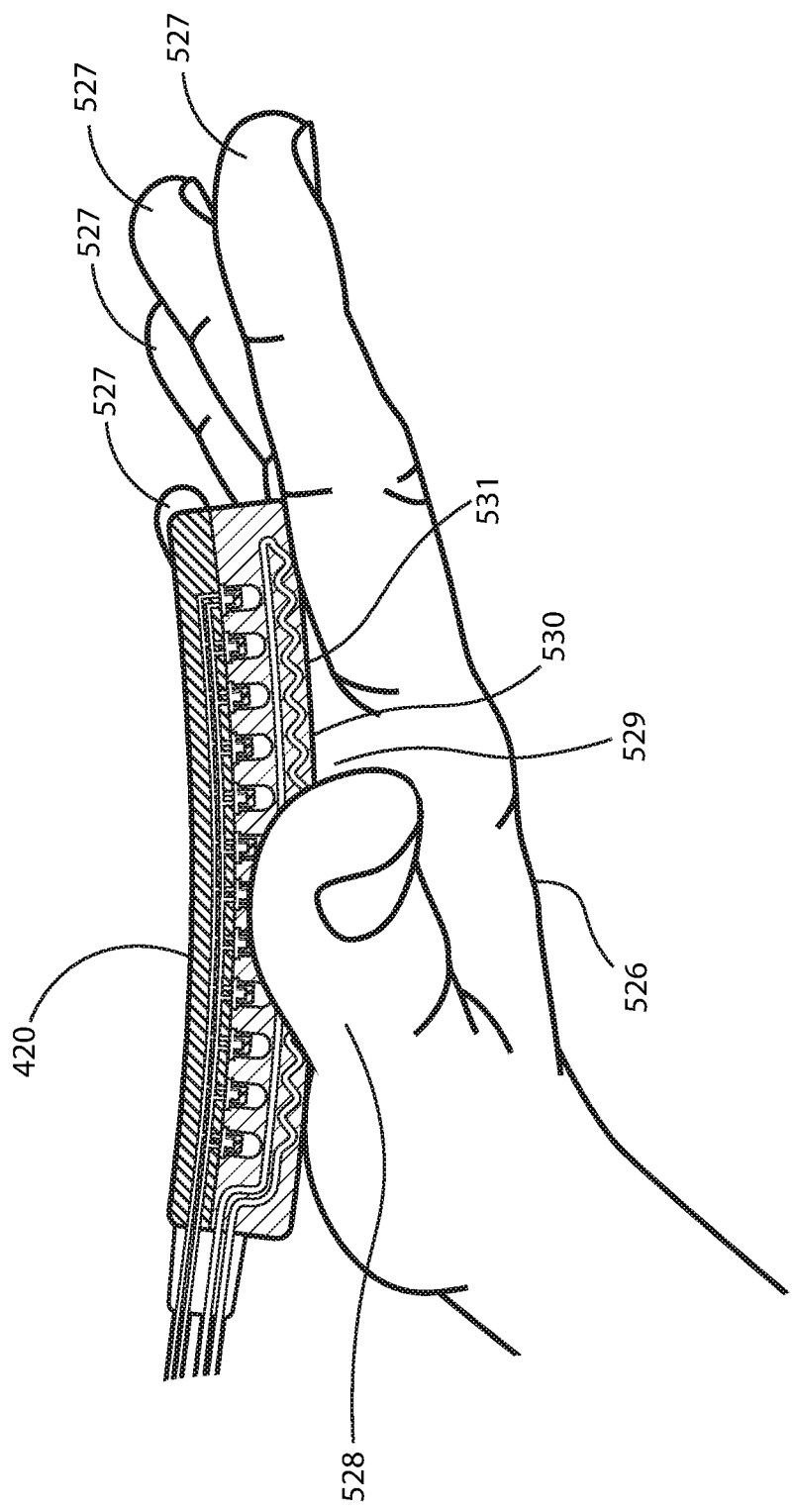
FIG. 5 illustrates the embodiment of the invention disclosed in FIG. 4 in contact with the palm of a human hand.

FIG. 5 illustrates the embodiment of the invention disclosed in FIG. 4 resting on the palm of a human hand. The representative view of human hand 526 containing fingers 527 and a thumb 528. One of ordinary skill in the art would recognize that while a human hand is illustrated in FIG. 5, the present invention will function when used in combination with any open skin area of any mammal and more preferably at a skin location with AVA blood vessels. For ease of reference, throughout this disclosure the mammal will be described as a human and the open skin area referenced will be that of a human hand.

During use in accordance with an embodiment of the present invention, the location of thermal transfer occurs at the interface between the surface of skin 530 and the surface 531 of module 420. Arteriovenous anastomoses 529 are located beneath the exterior surface of skin 530.

Figure 6:
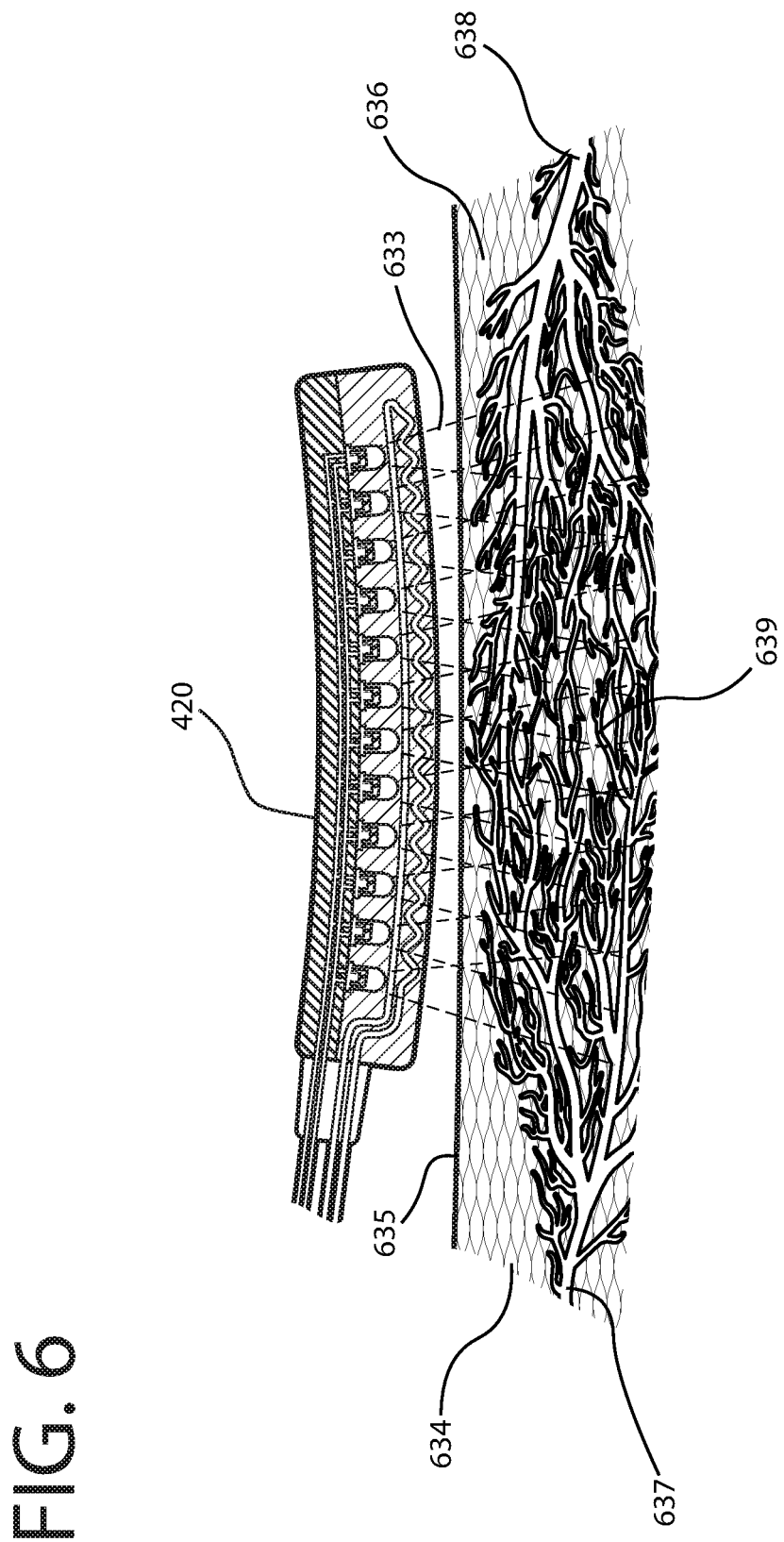
FIG. 6 illustrates the method of emission of infrared radiation through a translucent thermal transfer fluid bladder, through the surface of the skin, and into the arteriovenous anastomosis vasculature of the subjects, in accordance with this invention.

Turning to FIG. 6, a representative view of human anatomy and vasculature 634, such as located at the palm of a hand, is shown. The view contains the following anatomical features: interior dermal layer 635, sub dermal tissue 636, arterial blood supply 637, venous blood supply 638, and arteriovenous anastomoses blood vessels 639. A representative view of the path of infrared light 633 is shown as it exits module 420 through a translucent fluid bladder and bathes the arteriovenous anastomoses blood vessels 639. When treating for hyperthermia, blood exits the arterial supply at a temperature elevated above the body's desired homeostasis value, and enters the arteriovenous anastomoses blood vessels 639. Heat exchange occurs at the skin-module surface interface 531, shown in FIG. 5, due to the temperature differential between the blood and the fluid in the thermal transfer bladder 33, shown in FIGS. 2 and 3, which is conditioned to be at a temperature significantly lower than the user's current core temperature.

In an embodiment (not shown) a translucent substrate is located between the translucent fluid bladder and the skin surface. In embodiments the translucent substrate is rigid and non-flexible. In embodiments the translucent substrate is flexible and configured to conform to the palm or other open skin area of the human or other mammal.

As blood traverses through the arteriovenous anastomoses blood vessels 639, it loses thermal energy and thereby cools, entering the venous blood supply 638 at a temperature lower than when it exited the arterial blood supply 637. Infrared light 633 maximally vasodilates the arteriovenous anastomoses blood vessels 639, overriding the body's local thermoregulatory mechanism which would otherwise result in arteriovenous anastomoses closures, and thus maximizes thermal transfer of heat out of the body. Continuous flow of blood through this system, over time, reduces the core temperature of the human user, until a return to a state of thermal homeostasis occurs.

Figure 7:
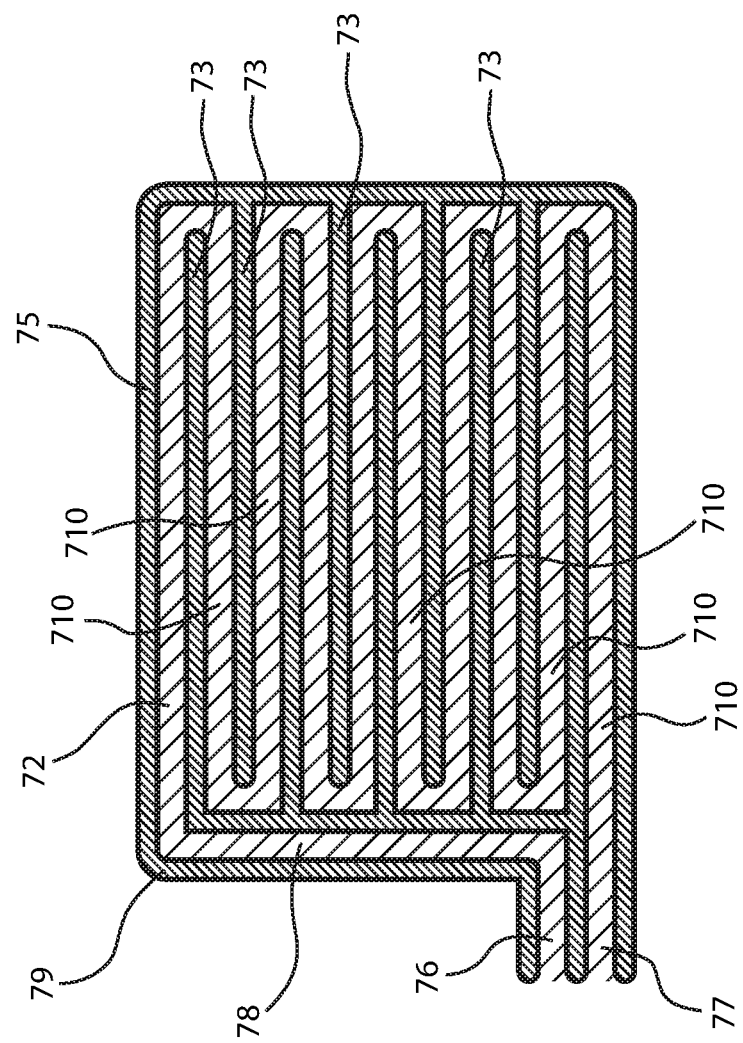
FIG. 7 illustrates the fluid path within a translucent thermal transfer fluid bladder made in accordance with this invention.

FIG. 7 is a schematic view along the vertical axis of a preferred embodiment of the invention illustrating the skin contacting surface 75 of the translucent thermal transfer fluid bladder 33 portion of the thermal exchange module 219 as shown in FIGS. 2 and 3. When used to reduce the core temperature of the body, such as during hyperthermia, thermal transfer fluid 72, preferably purified water, enters through the fluid inflow portion 76 of the bladder at a temperature substantially lower than the current core temperature of the user. The fluid follows a fluid path 78, bounded by outer portion 79, sealed between top and bottom surfaces of the fluid bladder, and enters into long fluid channels 710, which are defined by long portions 73, sealed between top and bottom surfaces of the fluid bladder. While fluid traverses the long fluid channels 710, thermal heat exchange occurs with the body, as described previously, through thermal interaction with the blood flowing through arteriovenous anastomoses blood vessels 639, shown in FIG. 6. The fluid exits the bladder through fluid outflow portion 77 at a temperature higher than when it entered the bladder through fluid inflow portion 76, having absorbed heat from the user's body. As described earlier, the fluid temperature is adjusted to a lower temperature, via a thermal conditioning unit, not shown, which exists in the fluid loop between the fluid outflow and fluid inflow portions.

Figure 8:
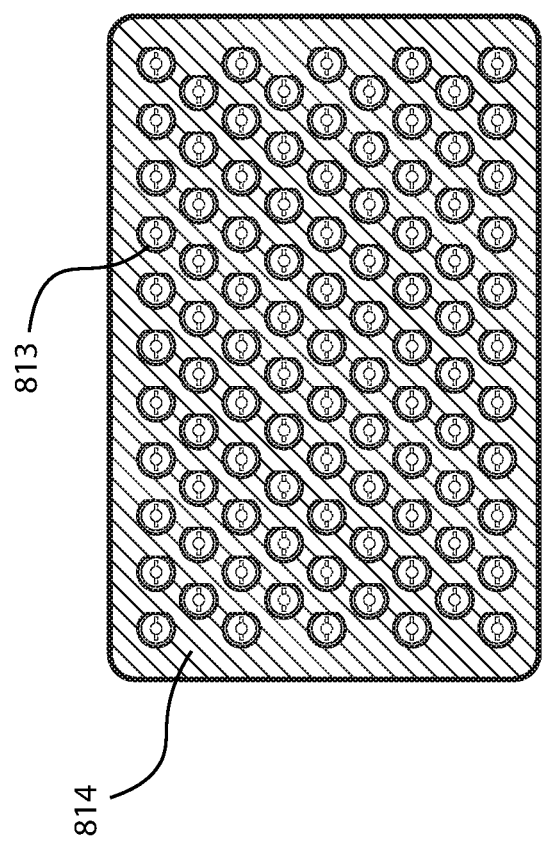
FIG. 8 illustrates an exemplary array of multiple light emitting diodes used to deliver the monochromatic infrared energy called for in the present invention.

FIG. 8 is a schematic view along the vertical axis of a preferred embodiment of central portion 311 of thermal exchange module 219, as shown in FIG. 3. Multiple near infrared light emitting diodes 813 are secured to a mounting panel 814, which contains required electrical circuitry (not shown). Diodes 813 emit near infrared light, which travels substantially through the translucent thermal transfer fluid bladder 33, shown in FIGS. 2 and 3, and exits the thermal exchange module 219. Near infrared light 633 (representatively depicted in FIG. 6) bathes the arteriovenous anastomoses blood vessels 639.

Figure 9:
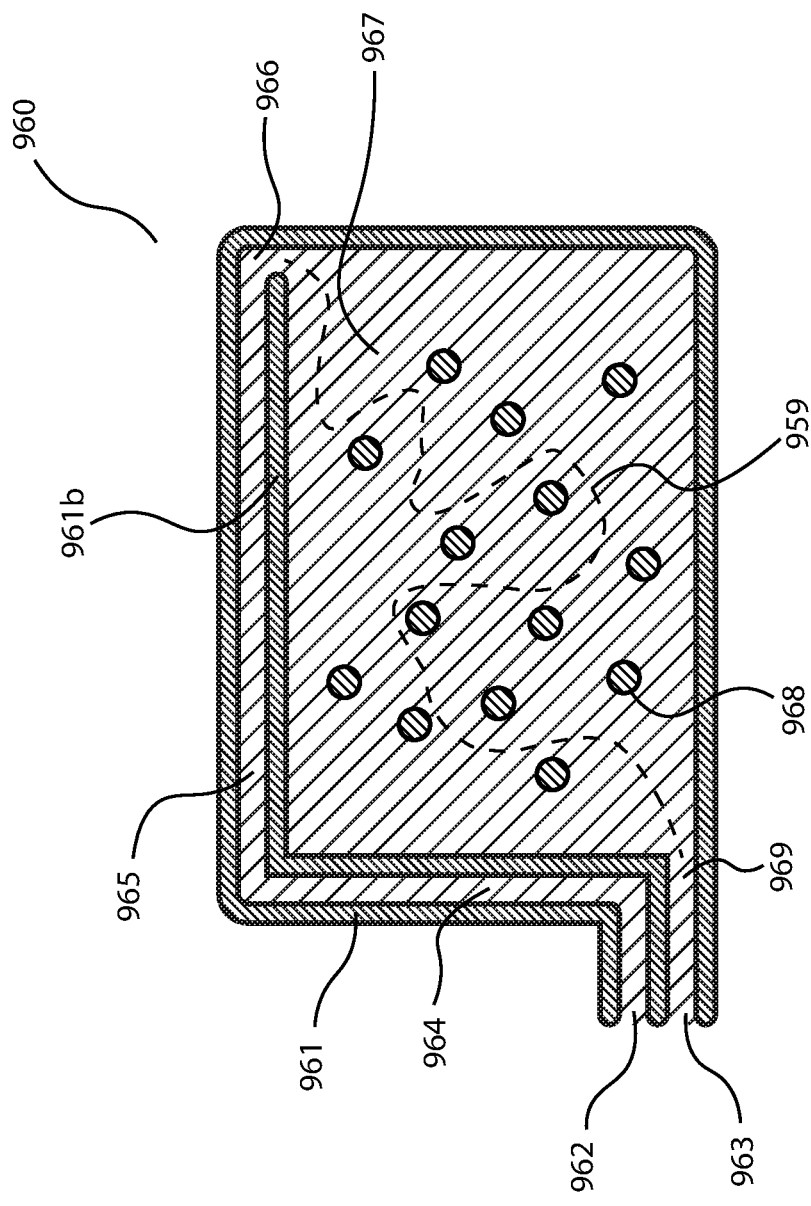
FIG. 9 illustrates the fluid path within an alternative embodiment of a translucent thermal transfer fluid bladder made in accordance with this invention.

FIG. 9 is a schematic view along the vertical axis of the skin-contacting surface of an alternative embodiment of a translucent thermal transfer fluid bladder 960 portion of a near infrared thermal exchange module 219 as shown in FIG. 2. Components include a sealed outer portion 961 between top and bottom surfaces of the fluid bladder, sealed inner portion 961b which separates fluid inflow portion 962 from fluid outflow portion 963 and defines long fluid path 964, and sealed post portions 968 between the top and bottom of the fluid bladder 960. During use, thermal transfer fluid 965, preferably purified water, enters through fluid inflow portion 962, follows long fluid path 964, encounters entry point 966 into to the main chamber 967 of the fluid bladder, and follows a randomized agitated path 959, shown here via representation only, due to the obstruction of post portions 968, until it reaches the main chamber exit point 969 and exits the bladder through the fluid outflow portion 963. As described earlier thermal transfer fluid 965 is conditioned by a thermal conditioning unit (not shown), which exists in the fluid loop between fluid outflow and fluid inflow portions. Thermal heat exchange occurs with the body, as described previously, while fluid 965 is traversing across chamber 967 along agitated path 959. The agitated path provides an alternative fluid flow mechanism as compared to long fluid channels 710 described in FIG. 7.

Figure 10:
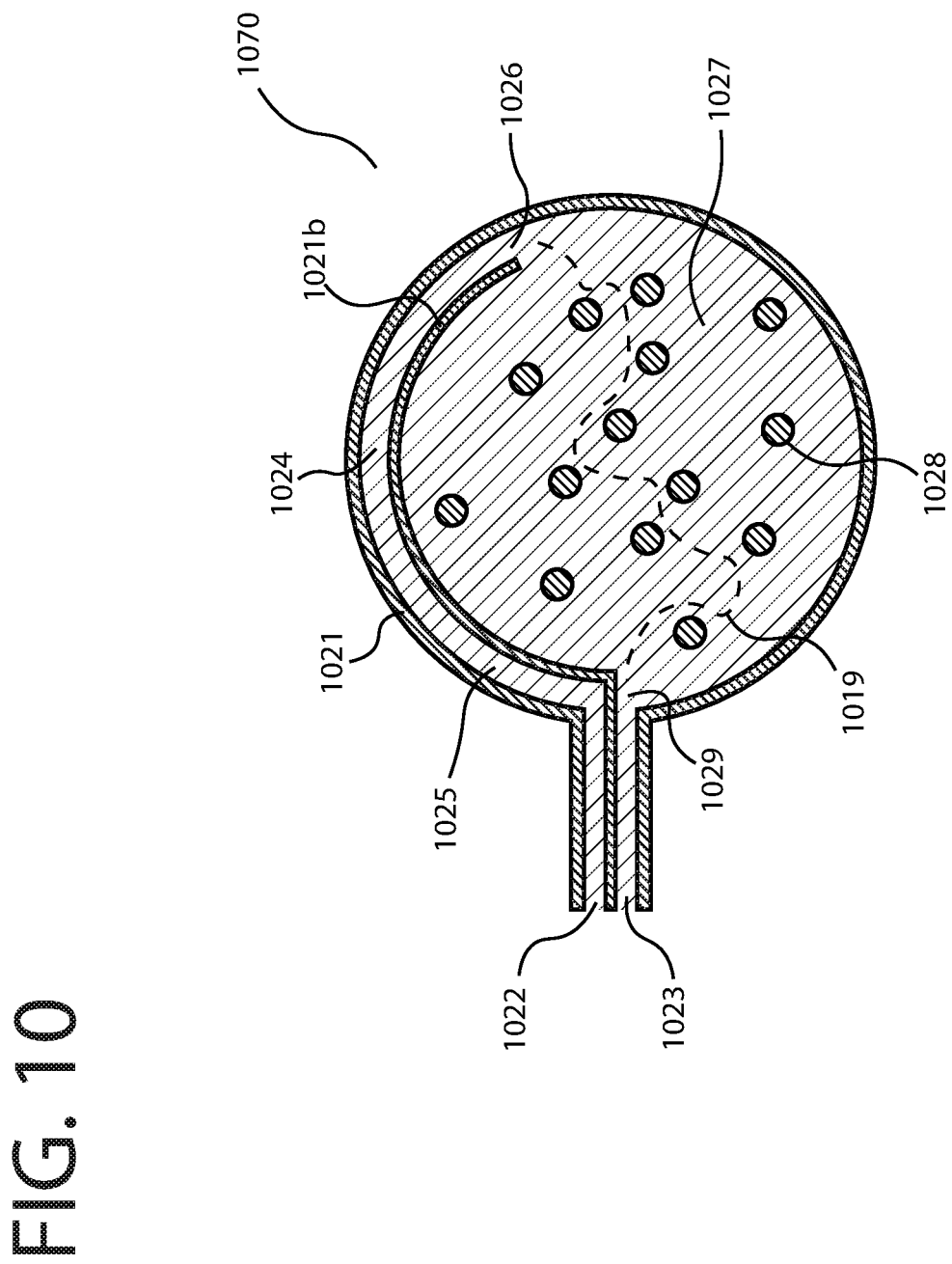
FIG. 10 illustrates a circular shaped translucent thermal transfer fluid bladder made in accordance with an alternative embodiment of this invention.

FIG. 10 is a schematic view along the vertical axis of the skin contacting surface of an alternative embodiment of a circular shaped translucent thermal transfer fluid bladder 1070 portion of a near infrared thermal exchange module, not shown, which is substantially also circular shaped. Similarly to the embodiment shown in FIG. 9, components include a sealed outer portion 1021 between the top and bottom surfaces of the fluid bladder, sealed inner portion 1021b which separates fluid inflow portion 1022 from fluid outflow portion 1023 and defines curved long fluid path 1024, and sealed post portions 1028 between top and bottom of fluid bladder 1070. During use, thermal transfer fluid 1025, preferably purified water, enters through fluid inflow portion 1022, follows curved long fluid path 1024, encounters entry point 1026 into to the main chamber 1027 of the fluid bladder, and follows a randomized agitated path 1019, shown here via representation only, due to the obstruction of post portions 1028, until it reaches the main chamber exit point 1029 and exits the bladder through the fluid outflow portion 1023. Thermal conditioning and heat exchange occur substantially as described previously for FIG. 9.

Figure 11:
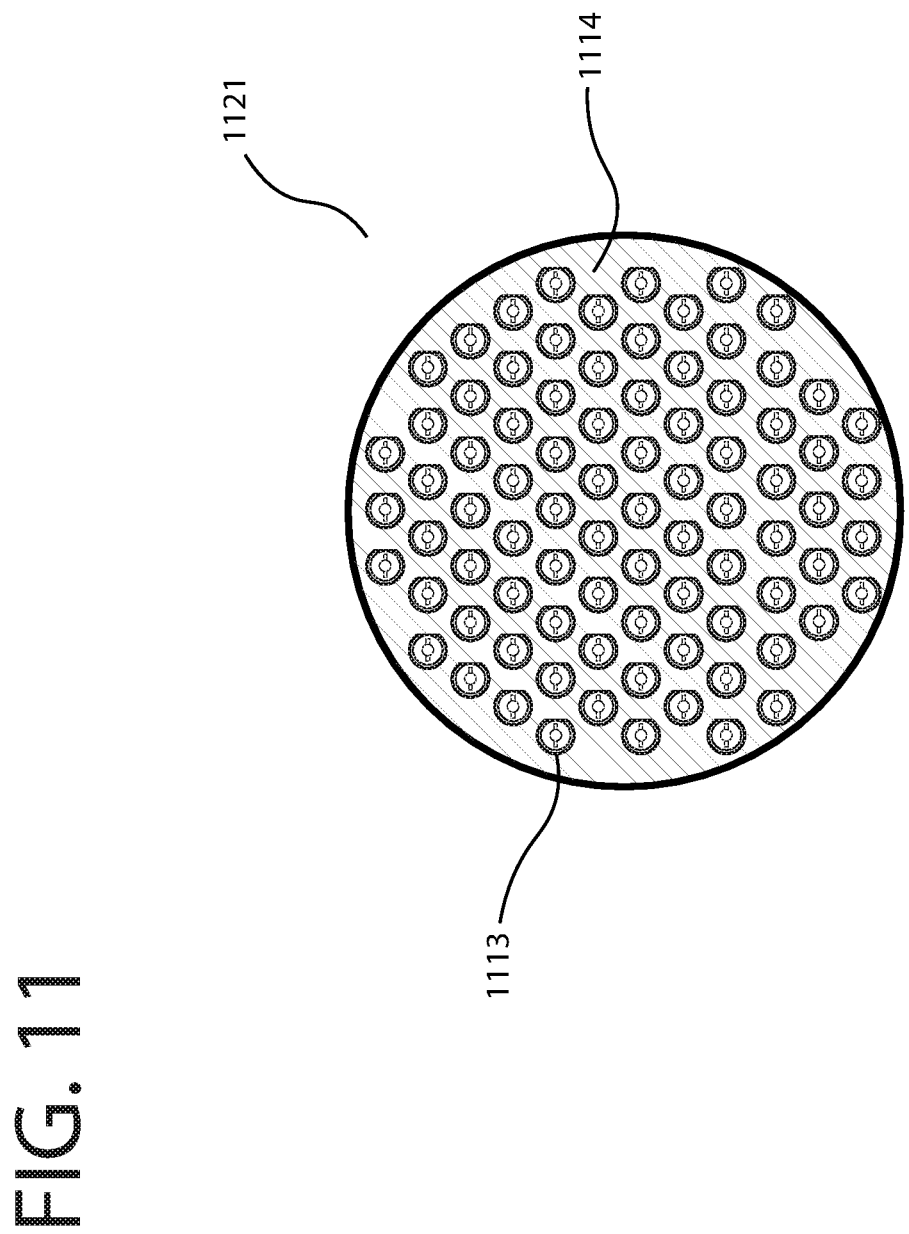
FIG. 11 illustrates a circular array of multiple light emitting diodes used to deliver the monochromatic infrared energy made in accordance with an alternative embodiment of this invention.

FIG. 11 is a schematic view along the vertical axis of an alternative embodiment of a circular shaped central portion 1121 of a near infrared thermal exchange module, not shown, which is substantially also circular shaped. Similarly to the embodiment shown in FIG. 8, multiple near infrared light emitting diodes 1113 are secured to a mounting panel 1114, which contains required electrical circuitry, not shown. The diodes emit near infrared light, which travels substantially through a circular shaped translucent thermal transfer fluid bladder 1070, such as shown in FIG. 10, and exits the circular-shaped thermal exchange module. Near infrared light 633 (representatively depicted in FIG. 6) bathes the arteriovenous anastomoses blood vessels 639.

Figure 12:
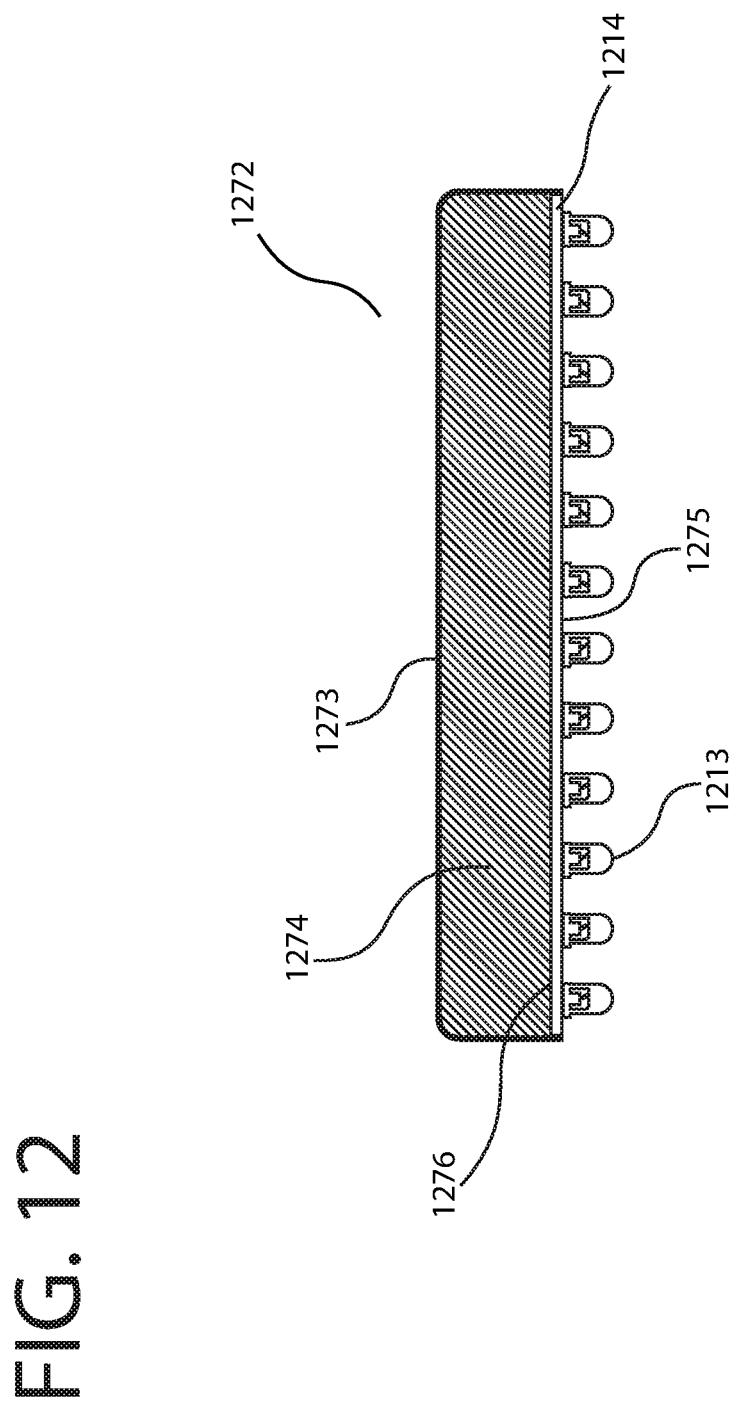
FIG. 12 illustrates a schematic cross-sectional view of a second alternate embodiment of this invention.

FIG. 12 is a schematic cross-sectional view of an alternate embodiment of a near infrared thermal exchange module 1272, wherein the thermal transfer mechanism between the module 1272 and user is provided primarily by a thermoelectric heat pump 1274, as opposed to the thermal transfer fluid bladder described in previous embodiments. In this embodiment, thermoelectric heat pump 1274 is contained within the outer casing 1273 of thermal exchange module 1272. The heat pump has a lower surface 1276, which maintains a temperature substantially different from the core temperature of the user, not shown. The temperature at lower surface 1276 drives the thermal transfer between the module and the user, through applicable conditioning of the temperature of the components located on the skin contacting side 1275 of the module. Applicable control electronics, not shown, and power supply, not shown, both of which would be apparent to one skilled in the art, may also be contained within outer casing 1273. Alternatively, control electronics and power supply may be contained external to outer casing 1273, connected via sufficient electronic cabling, not shown, which would be apparent to one skilled in the art. In this alternate configuration, multiple near infrared light emitting diodes 1213 are secured to a mounting panel 1214, which contains required electrical circuitry, not shown. The diodes and mounting panel are located on skin contacting side 1275 of thermal exchange module 1272. The diodes emit near infrared light and increase blood flow in the arteriovenous anastomoses blood vessels, as described earlier. Heat exchange occurs at the skin-module surface interface, not shown, due to the temperature differential between the blood and skin contacting side of the thermal exchange module.

Figure 13:
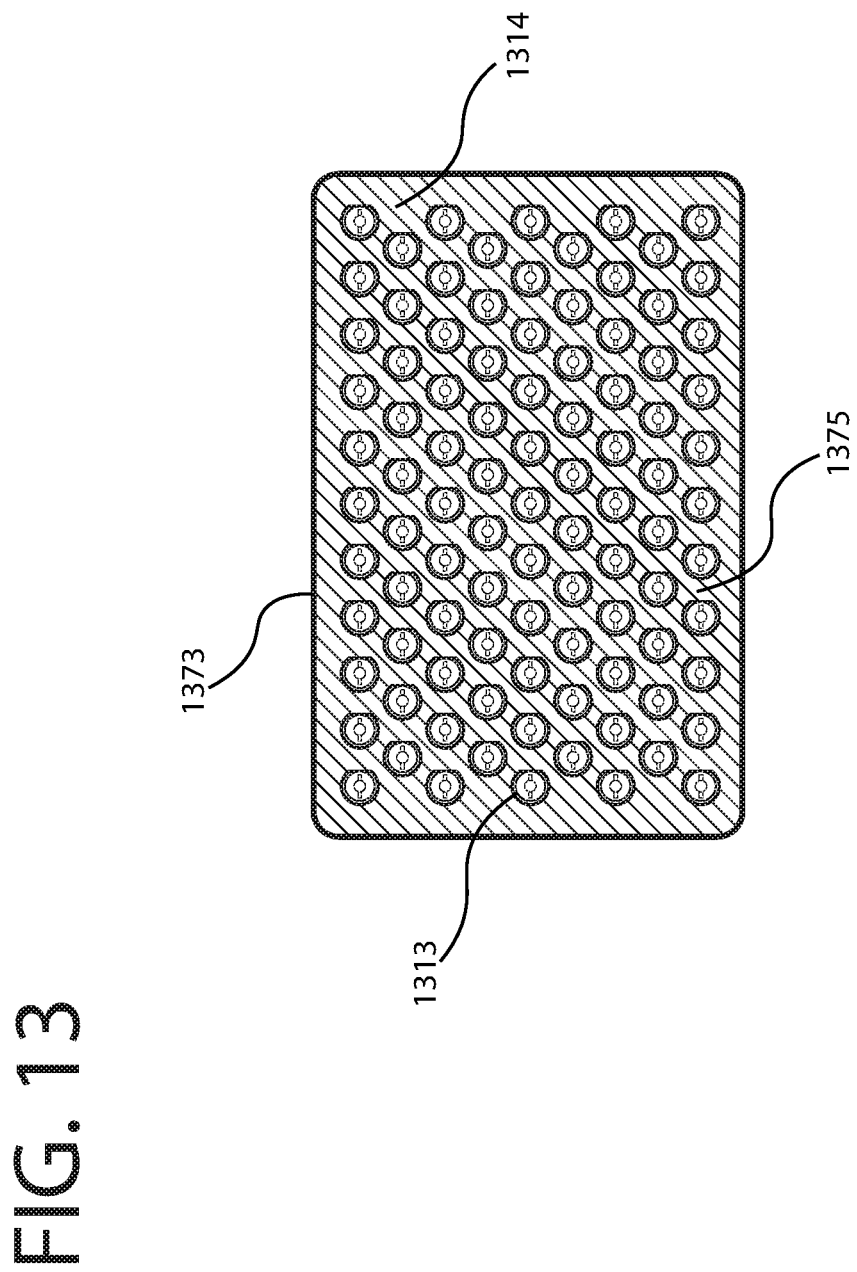
FIG. 13 illustrates a schematic view along the vertical axis of the alternative embodiment shown in FIG. 12.

FIG. 13 is a schematic view along the vertical axis of the alternative embodiment 1272 of a near infrared thermal exchange module which is shown in FIG. 12. Outer casing 1373 contains the thermoelectric heat pump, not shown. Multiple near infrared light emitting diodes 1313 are secured to a mounting panel 1314, which contains required electrical circuitry, not shown. The diodes and mounting panel are located on skin contacting side 1375 of the thermal exchange module 1272. Although the outline of the module is shown to be generally rectangular, it would be obvious to one skilled in the art that the outline of the module may take a variety of shapes, such as circular, hexagonal, square, and others.

Figure 14A:
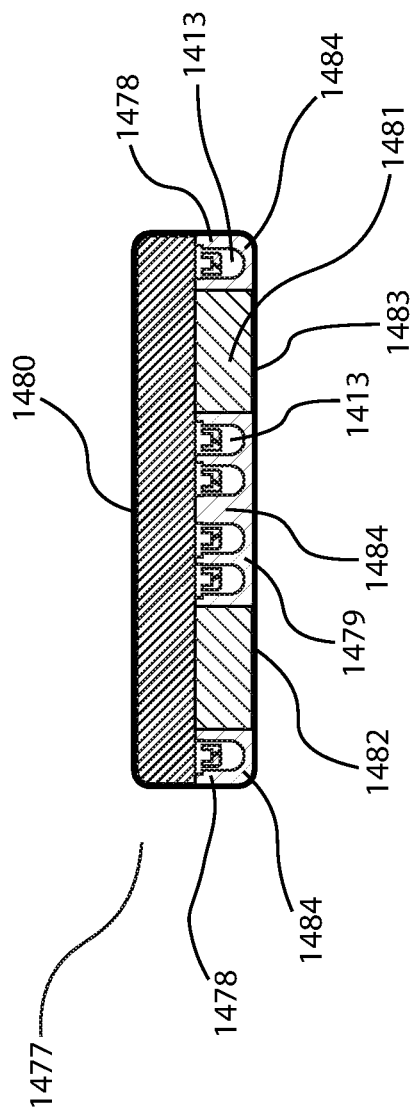
FIG. 14a illustrates a schematic cross-sectional view of a third alternate embodiment of this invention.
Figure 14B:
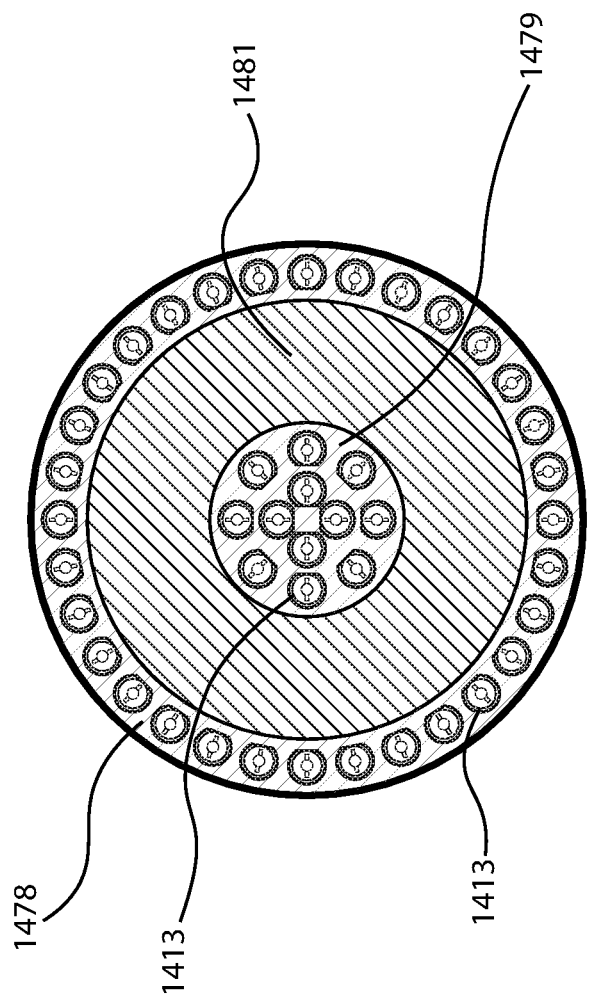

An alternative embodiment of a near infrared thermal exchange module 1477, wherein the thermal transfer mechanism between the module and a user is provided primarily by a thermoelectric heat pump, is shown in FIGS. 14a and 14b. FIG. 14a is a schematic cross-sectional view of the near infrared thermal exchange module. FIG. 14b is a schematic view along the vertical axis of the module, presenting a view of the skin contacting surface 1483. The module is generally circular in shape, and includes an inner circular location 1479 of multiple near infrared light emitting diodes 1413 and an outer ring-shaped location 1478 of multiple diodes 1413. The diodes are contained within a generally translucent encasement 1484, which can be made of glass, plastics, quartz, or any material available to one skilled in the art that allows transmittance of near infrared light. In this configuration, an annular shaped thermoelectric heat pump 1481 generates the transfer of heat to or from the user, at the thermal transfer interface 1482, along the plane of skin contact 1483 with the user, not shown. Module 1477 is encased within an outer casing 1480, which also contains electronics, systems, and power supply, collectively not shown, which would be apparent to one skilled in the art.

Figure 15:
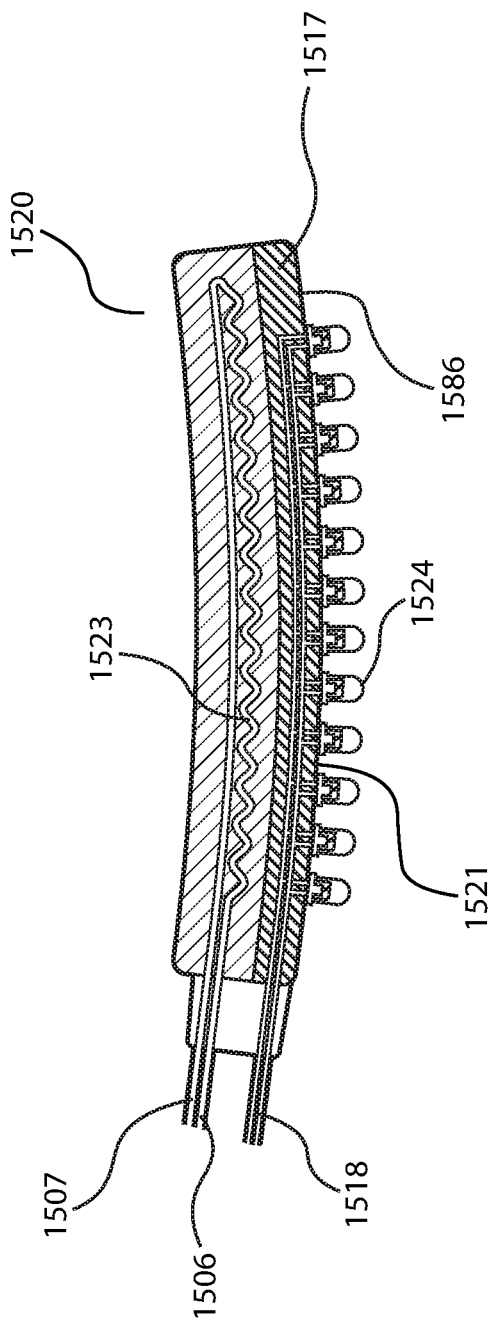
FIG. 15 illustrates a schematic cross-sectional view of a fourth alternate embodiment of this invention.

In an alternative embodiment to the near infrared thermal exchange module as described in FIG. 4, the near infrared light source is located at the skin contacting surface and the thermal transfer bladder is located behind the near infrared light source, as shown in a schematic cross-sectional view of the near infrared thermal exchange module 1520 illustrated in FIG. 15. In this embodiment, the skin contacting surface 1586 of the module contains a preferred curved surface 1521, defined by an electronics housing module 1517, upon which are mounted multiple near infrared light emitting diodes 1524. The diodes are connected to an external power source (not shown) via current carrying electrical cable 1518. In this schematic view the thermal transfer fluid bladder 1523, which need not be translucent, is located atop housing module 1517. In this alternative embodiment, thermal exchange occurs between fluid bladder 1523 and housing module 1517, and between housing module 1517 and the skin of the user (not shown), at skin contacting surface 1586. As such, housing module 1517 acts as a thermal transfer conduit between fluid bladder 1523 and the skin of the user.

Figure 16:
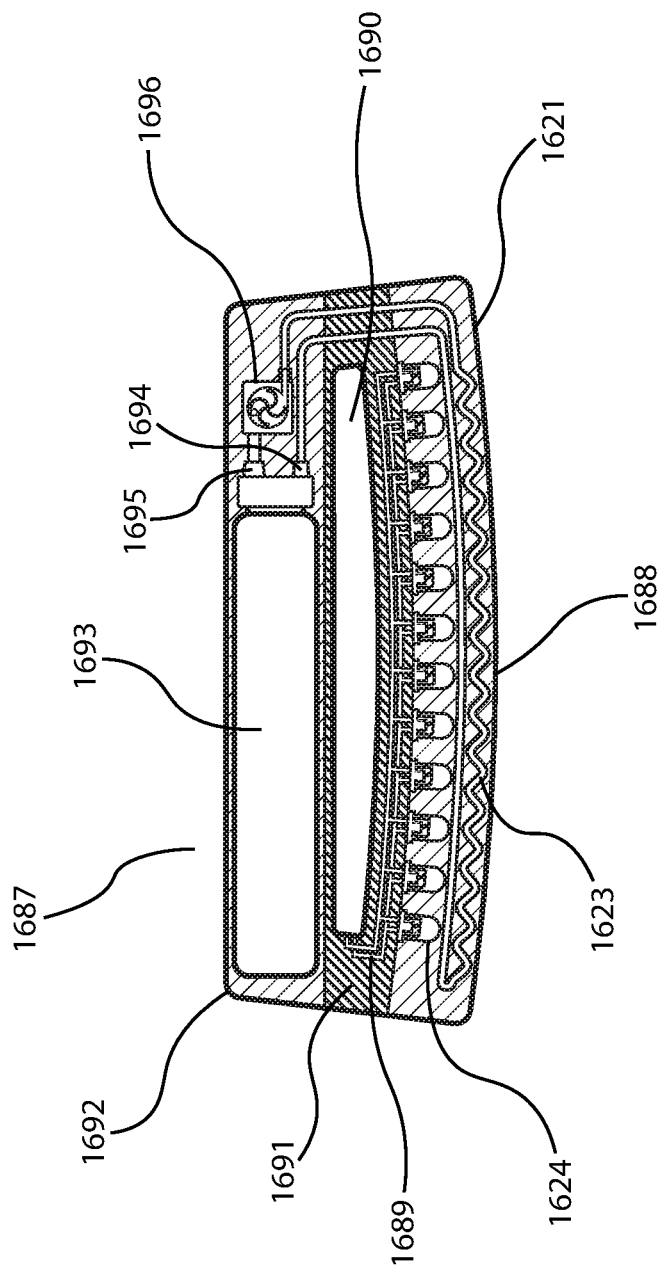
FIG. 16 illustrates a schematic cross-sectional view of a fifth alternate embodiment of this invention.

FIG. 16 is a schematic cross-sectional view of an alternative embodiment of a near infrared thermal exchange module 1687, wherein a modular power supply 1690 and thermal conditioning fluid chamber 1693 are both encapsulated within the housing 1692 of thermal exchange module 1687. In this embodiment, multiple near infrared light emitting diodes 1624 are mounted to an electrical component housing module 1691, and connected to power supply 1690 via electrical connections 1689, the power supply and electrical connections both contained within electrical component housing module 1691. Translucent thermal transfer fluid bladder 1623 transfers fluid, not shown, to thermal conditioning fluid chamber 1693 via fluid chamber inflow connection 1694. The fluid exits fluid chamber 1693 after thermal conditioning via fluid chamber outflow connection 1695, drawn via force from fluid flow pump mechanism 1696 shown in schematic form, before returning to fluid bladder 1623. Fluid bladder 1623 has an external skin contacting surface 1688 along a preferred curved surface 1621.

Figure 17:
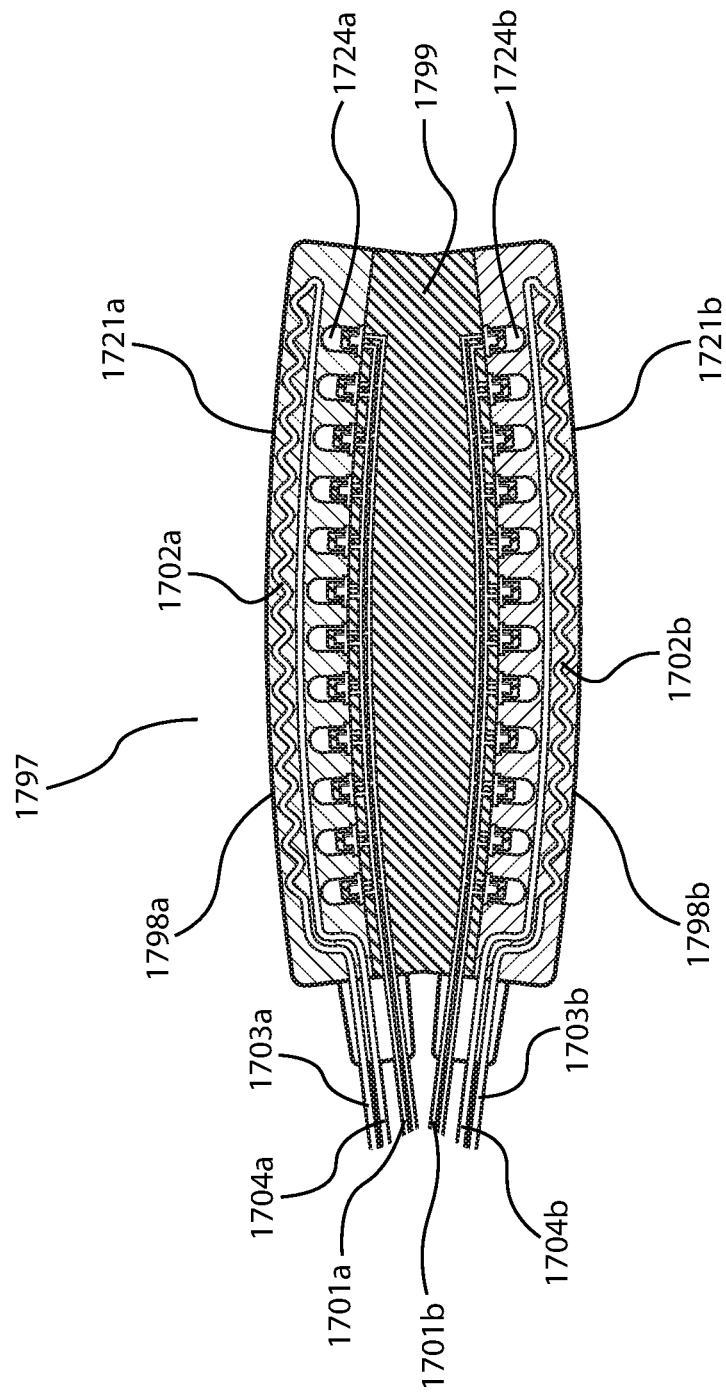
FIG. 17. illustrates a schematic cross-sectional view of a sixth alternate embodiment of this invention.

In an alternative embodiment shown in the schematic cross-sectional view of FIG. 17, a near infrared thermal exchange module 1797 contains two skin contacting surfaces 1798a and 1798b. In such an embodiment, heat exchange between the user and module 1797 can occur simultaneously at two surfaces, for example the palm of the left hand and palm of the right hand, approximately doubling the rate of heat exchange experienced by the user compared to a near infrared thermal exchange module with a single skin contacting surface. In this alternative embodiment, multiple near infrared light emitting diodes 1724a are mounted to an electronic housing element 1799 inwardly located on module 1797. Diodes 1724a are connected to an external power source (not shown) via current carrying electrical cable 1701a. Similarly, a secondary group of multiple near infrared light emitting diodes 1724b are mounted to electronic housing element 1799. The diodes are connected to an external power source (not shown) via current carrying electrical cable 1701b, and oriented such that their emitted light is directionally opposite of emitted light from oppositely mounted light emitting diodes 1724a. Additionally, translucent thermal transfer fluid bladder 1702a is connected to an external fluid conditioning unit, not shown, via fluid inflow portion 1703a and fluid outflow portion 1704a. Fluid bladder 1702a has an external skin contacting surface which is coincident with skin contacting surface 1798a, along a preferred curved surface 1721a. Similarly, secondary translucent thermal transfer fluid bladder 1702b is connected to an external fluid conditioning unit, not shown, via fluid inflow portion 1703b and fluid outflow portion 1704b. Secondary fluid bladder 1702b has an external skin contacting surface which is coincident with skin contacting surface 1798b, along a secondary preferred curved surface 1721b. In an embodiment, fluid bladder 1702a and fluid bladder 1702b are supplied with fluid by the same fluid conditioning unit.

Figure 18:
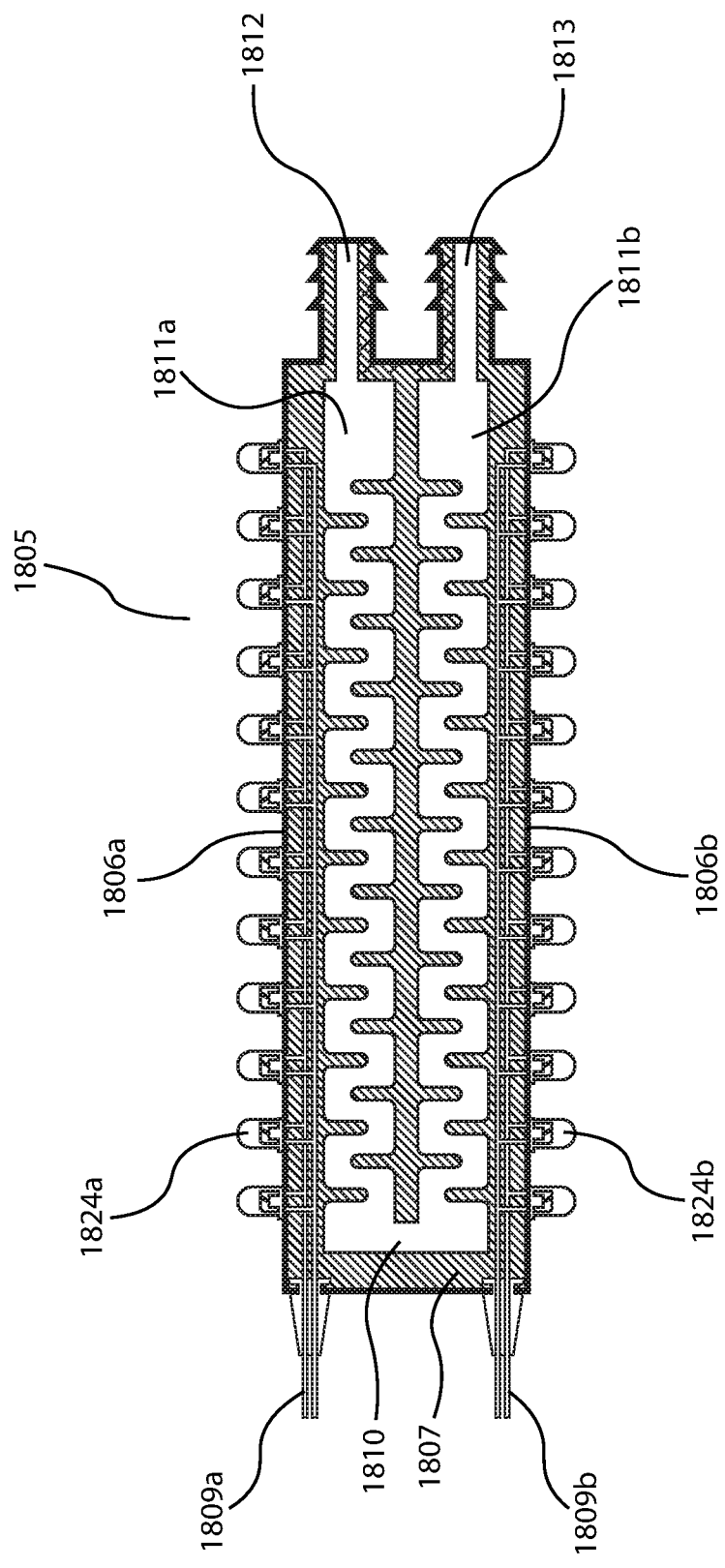
FIG. 18. illustrates a schematic cross-sectional view of a seventh alternate embodiment of this invention.

FIG. 18 illustrates an alternative embodiment for a near infrared thermal exchange module 1805 with two skin contacting surfaces 1806a and 1806b. In this exemplary embodiment, the thermal transfer fluid bladder, shown in a schematic cross section 1810, contains upper 1811a and lower 1811b thermal transfer fluid channels. Fluid bladder 1810 is connected to an external fluid conditioning unit, not shown, via fluid inflow portion 1812 and fluid outflow portion 1813. Additionally, multiple near infrared light emitting diodes 1824a are mounted to a housing element 1807. Diodes 1824a are connected to an external power source (not shown) via current carrying electrical cable 1809a. Similarly, multiple near infrared light emitting diodes 1824b are mounted to housing element 1807. Diodes 1824b are connected to an external power source (not shown) via current carrying electrical cable 1809b, and oriented such that their emitted light is directionally opposite of emitted light from oppositely mounted light emitting diodes 1824a. In this embodiment the thermal transfer fluid bladder 1810 is contained within the housing element 1807, and thermal exchange occurs between fluid bladder 1810 and housing element 1807, and between housing element 1807 and skin of the user (not shown), at skin contacting surfaces 1806a and 1806b. As such, housing element 1807 acts as a thermal transfer conduit between fluid bladder 1810 and the skin of the user. Advantages of this embodiment include two skin contacting surfaces and the need for only one thermal transfer fluid bladder, which may reduce complexity.

Figure 19:
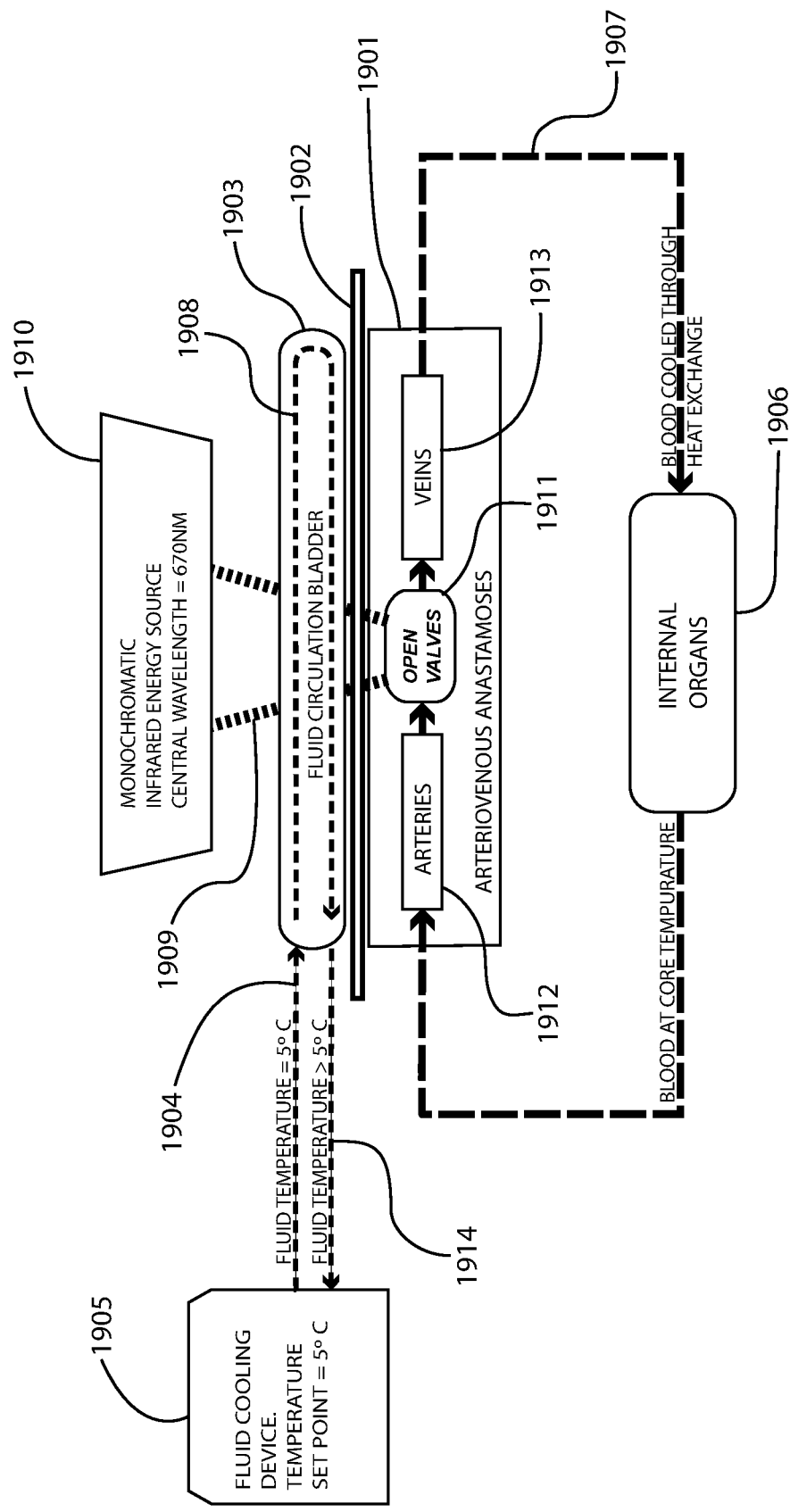
FIG. 19. illustrates a block diagram of an exemplary embodiment of the method disclosed.

In an exemplary embodiment of a method carried out in accordance with this invention, as shown in diagram form depicted in FIG. 19, heat energy is removed from the human circulatory vasculature, specifically at the location of the arteriovenous anastomoses (AVA) 1901. This is accomplished utilizing direct contact between the dermal layer 1902 of the palm of the hand and a heat transfer mechanism, consisting of a circulating fluid 1908 enclosed in a thin translucent bladder 1903, the fluid being constantly replenished externally with fluid 1904 at a set temperature that is significantly lower than 37° C. (98.6° F.), cooled by an external fluid cooling device 1905. In this exemplary embodiment, the fluid cooling device temperature set point is 5° C.

The human circulatory system carries the decrease in thermal energy to the body's core internal organs 1906, through utilization of blood 1907 that is at a lower temperature when it leaves the AVA structures than when it arrived, thus lowering the core body temperature in a rapid fashion. The palm of the hand is bathed in electromagnetic radiation 1909, provided by a MIRE light emitting diode array 1910 with, in this embodiment, a central wavelength of 670 nm, which penetrates through the translucent fluid bladder 1903 and into the AVA vasculature 1901 of the hand, beneath the surface of the palm. This infrared energy exposure overrides the local thermoregulatory response, forcing AVA valves 1911 to remain in an open state, creating sustained vasodilation and increased blood flow in the AVA vasculature, specifically in arteries 1912 and veins 1913, amplifying and sustaining the transfer of heat away from the core organs and out of the human body, through the warmed fluid 1914 of the heat transfer mechanism, which is then cooled in external fluid cooling device 1905 before returning towards the heat transfer mechanism and starting the cycle again.

In an alternative embodiment of a method carried out in accordance with the present invention (not shown), the whole hand or partial hand is immersed in a cold-water bath, ice bath, or cold-water jacketing device to remove heat energy from the AVA vasculature while the palm is exposed to the monochromatic infrared energy light source.

SUMMARY OF TEST RESULTS

Two physiological tests were performed on human subjects, to illustrate the reduction in core temperature after physical exertion when carrying out the method of the present invention.

The first test, performed on one subject, consisted of a control trial and a treatment trial, separated by approximately 24 hours. Each trial consisted of two phases: exercise and recovery. The subject was monitored for core temperature, measured rectally, during the exercise and recovery phases.

The exercise phase of the control trial consisted of elevated physical exertion, during which the subject rode a stationary cycle ergometer for 20 minutes in a thermally-raised enclosure. A sustained core temperature of approximately 38.0° C. (100.4° F.) was attained. The recovery phase of the control trial consisted of seated rest for 20 minutes in a climate-controlled room at approximately 23° C. (73.4° F.) and 50% relative humidity, with no treatment applied.

Figure 20:
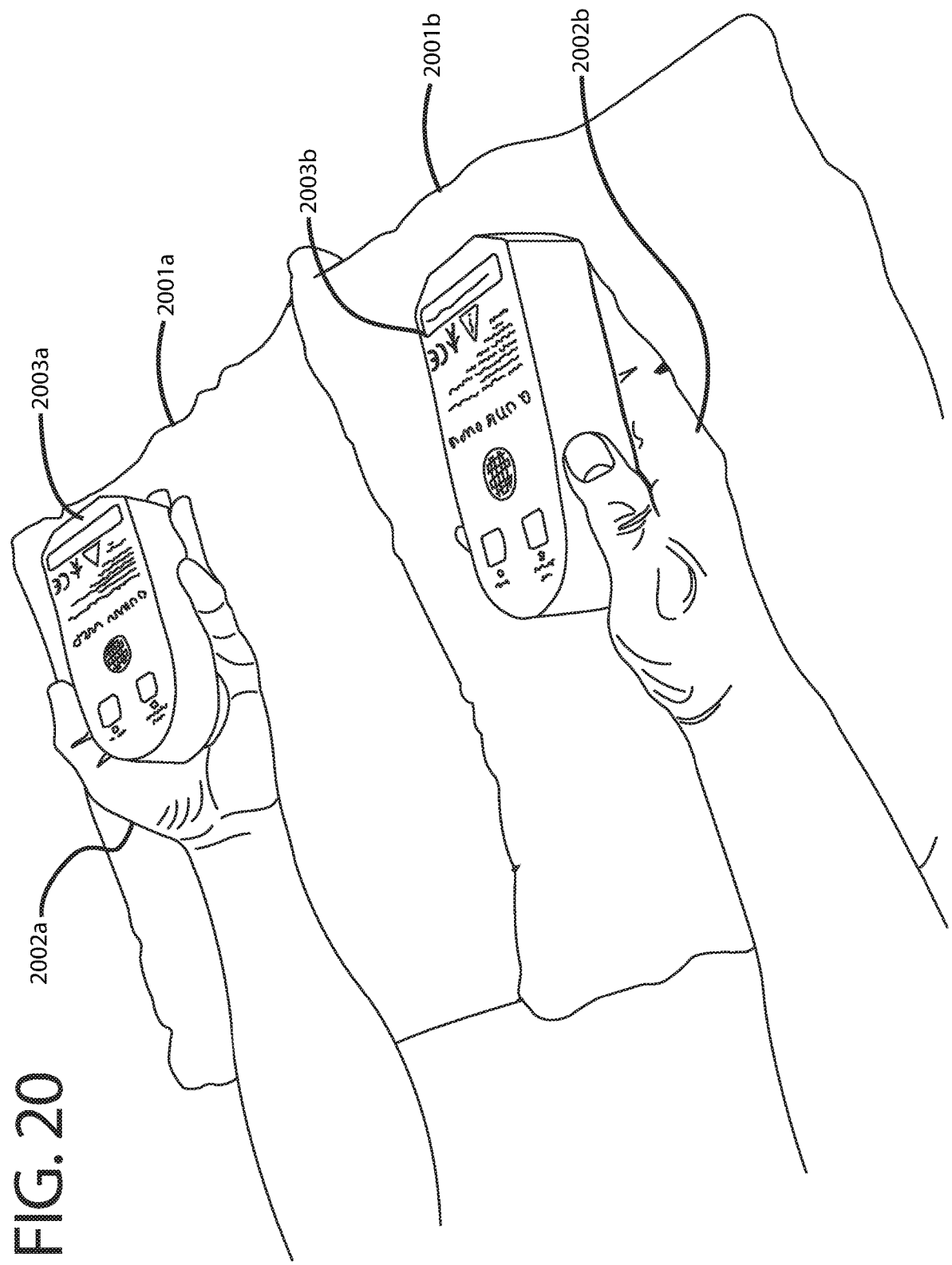
FIG. 20 illustrates the lower arm and hand positioning during a test method used to investigate the feasibility of the claimed method.
Figure 21:
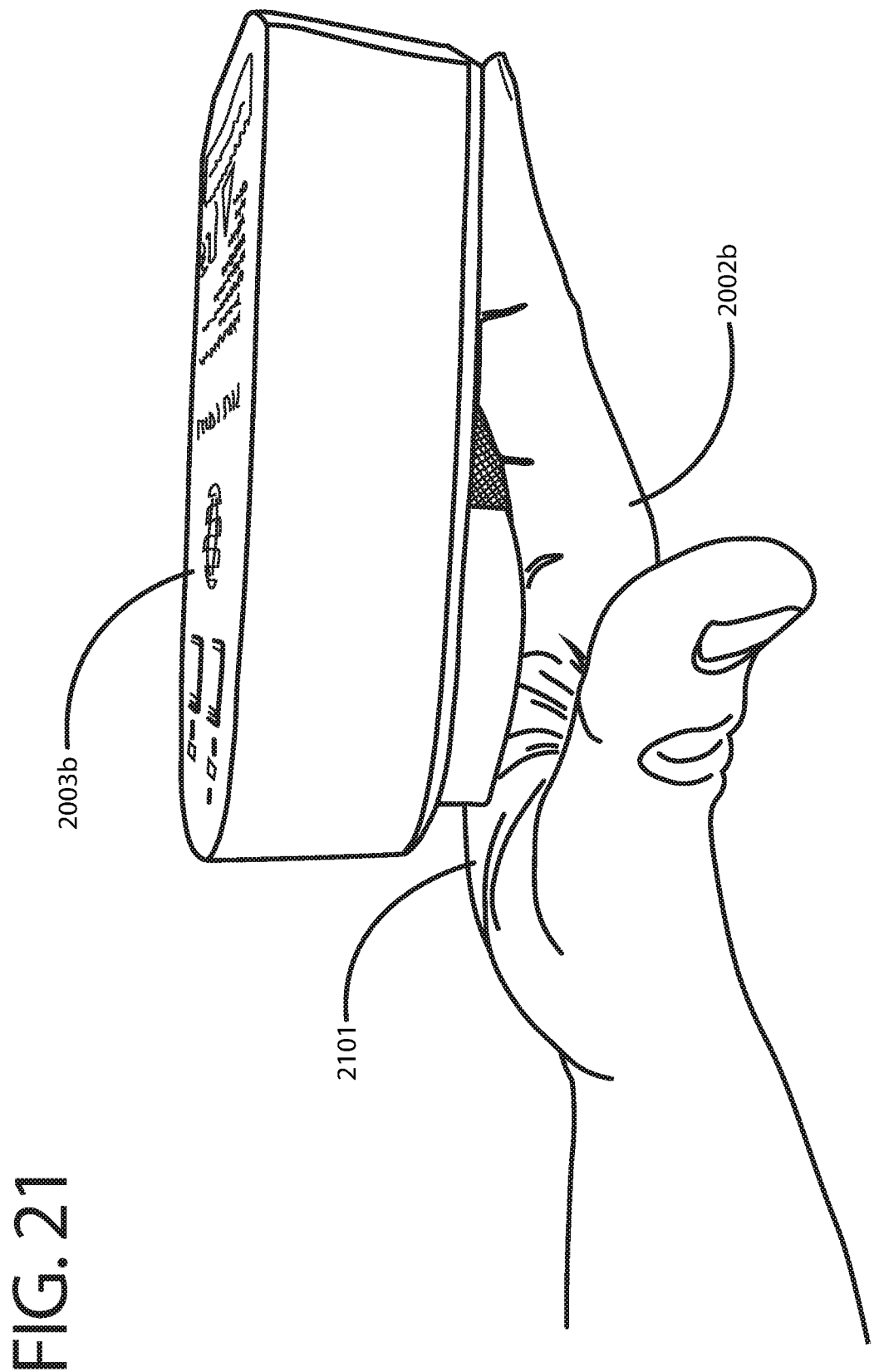
FIG. 21 illustrates a close-up view of the right-hand positioning during the test method described in FIG. 20.

The exercise phase of the treatment trial consisted of the same level of elevated physical exertion, during which the subject rode a stationary cycle ergometer for 20 minutes in a thermally-raised enclosure, and a sustained core temperature of approximately 38.0° C. (100.4° F.) was attained. The recovery phase of the treatment trial consisted of seated rest for 20 minutes in a climate-controlled room at approximately 23° C. (73.4° F.) and 50% relative humidity. During the recovery phase, as shown in FIG. 20, the subject's left hand 2002a and right hand 2002b rested, respectively, on top of polyethylene bags 2001a and 2001b filled with crushed ice, with the back and sides of the hands directly contacting the bags of ice. Devices 2003a and 2003b were placed on the palm of each hand. Each device contained a light emitting diode array, providing monochromatic infrared energy with a width from 620 nm to 720 nm and a peak central wavelength of 670 nm, a light intensity of 50 mw/cm$^2$, and a radiation area of 7.5 cm$^2$ (WARP 10A, supplied by Quantum Devices, Barneveld, Wis.). As shown in FIG. 21, the radiant infrared energy was directed toward approximately the center of the palm 2101 of the right hand 2002b. Utilizing this methodology, monochromatic infrared energy penetrated the palm of the hand and interacted with blood hemoglobin and arteriovenous anastomosis vasculature, as illustrated in FIG. 1. The infrared exposure was constant throughout the 20 minutes of the recovery phase of the treatment trial.

Figure 26:
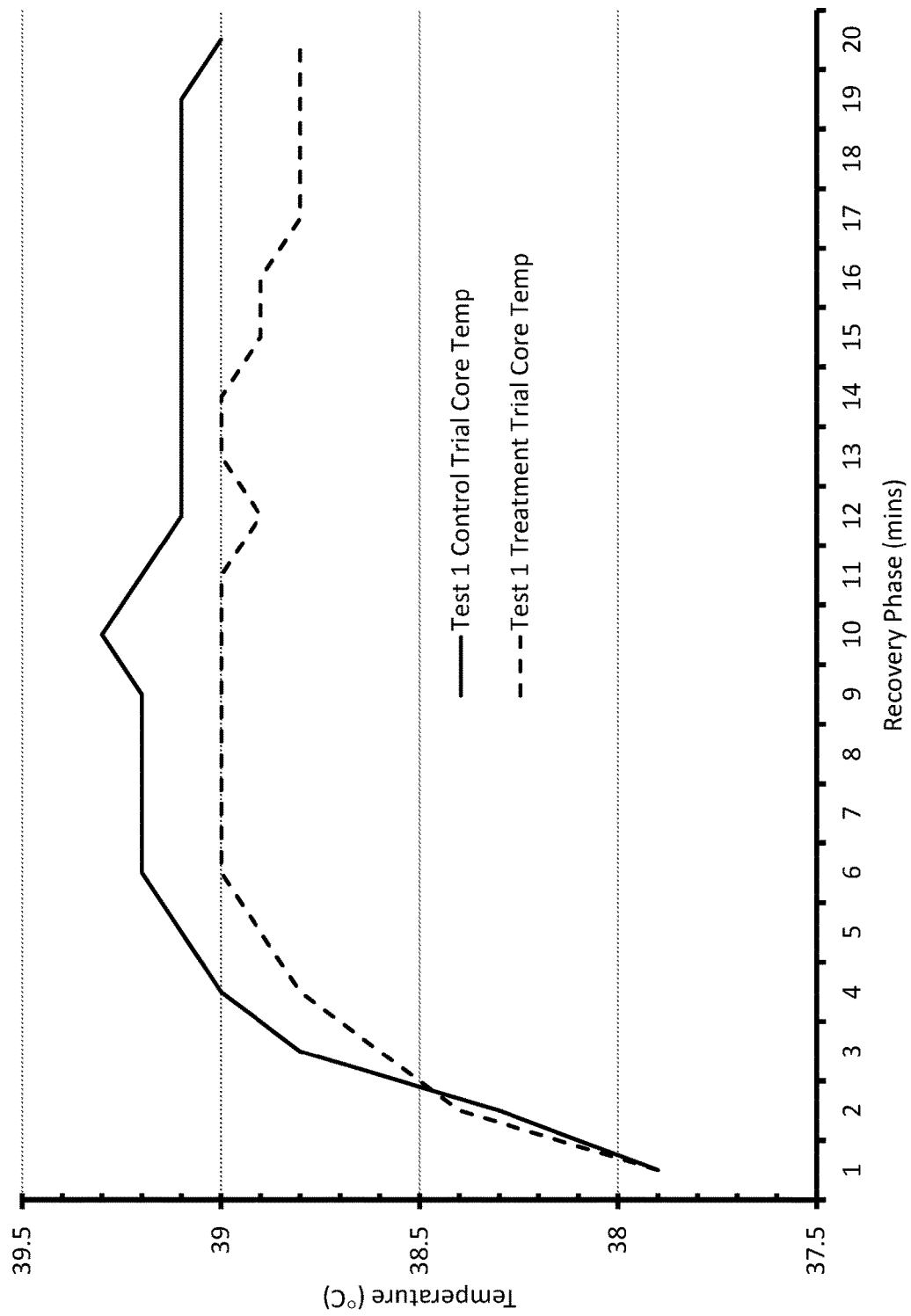
FIG. 26 illustrates the results as they pertain to core temperature of the control trial and treatment trial of the test method described in FIG. 20.

Results of the first test, as seen in FIG. 26, demonstrated a rapid rise of core temperature at the start of the recovery phase during both the control trial and the treatment trial. This is a common post-exercise phenomenon. During the treatment trial the subject experienced a relative difference in core temperature of −0.2 to −0.3° C. (−0.4 to −0.5° F.), compared to the control trial. This relative difference was attained within the first four minutes of the treatment trial, and was sustained for the remainder of the recovery phase.

During the second physiological test, performed on three human subjects, the core body temperature was cooled during the recovery period of the treatment trial, utilizing components of the apparatus shown in FIG. 2 and FIG. 3. In the second test, the hands were exposed to cold temperatures during the recovery phase of both the control trial and the treatment trial by exposing the back of the hand and the palm to cold temperatures. Skin surface temperature measurements were also taken during the recovery phase.

The second test was designed such that the only difference between the control trial and the treatment trial was palm exposure to infrared energy.

The second test consisted of a control trial and a treatment trial, separated by approximately four hours. Each trial consisted of two phases: exercise and recovery. The subjects were monitored for core temperature, measured rectally, during the exercise and recovery phases.

The exercise phase of the control trial consisted of elevated physical exertion, during which each subject rode a stationary cycle ergometer in a thermally-raised enclosure, just long enough for the subject to experience an elevation in core temperature of 0.5° C. (0.9° F.), approximately 3 to 5 minutes.

Figure 22:
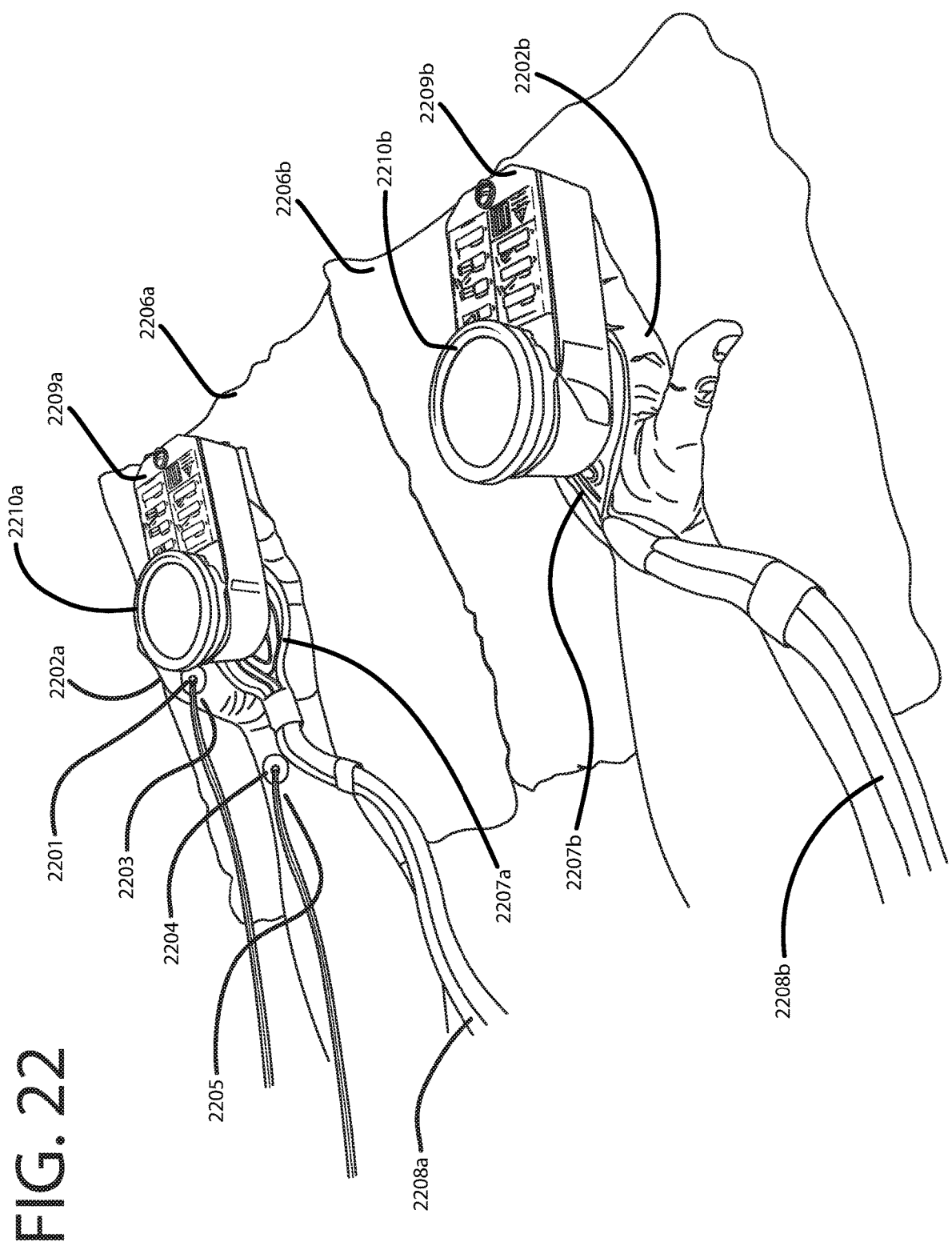
FIG. 22 illustrates the lower arm and hand positioning during the control trial of a second test method used to investigate the feasibility of the claimed method.

At the beginning of the recovery phase of the control trial, as shown in FIG. 22, one temperature sensor 2201 was placed on the palm side of the left hand 2202a, approximately located at the thenar eminence 2203. A second temperature sensor 2204 was placed on approximately the center of the left wrist 2205, palm side. Skin temperature at these locations was monitored during the recovery phase of the control trial.

Figure 23:
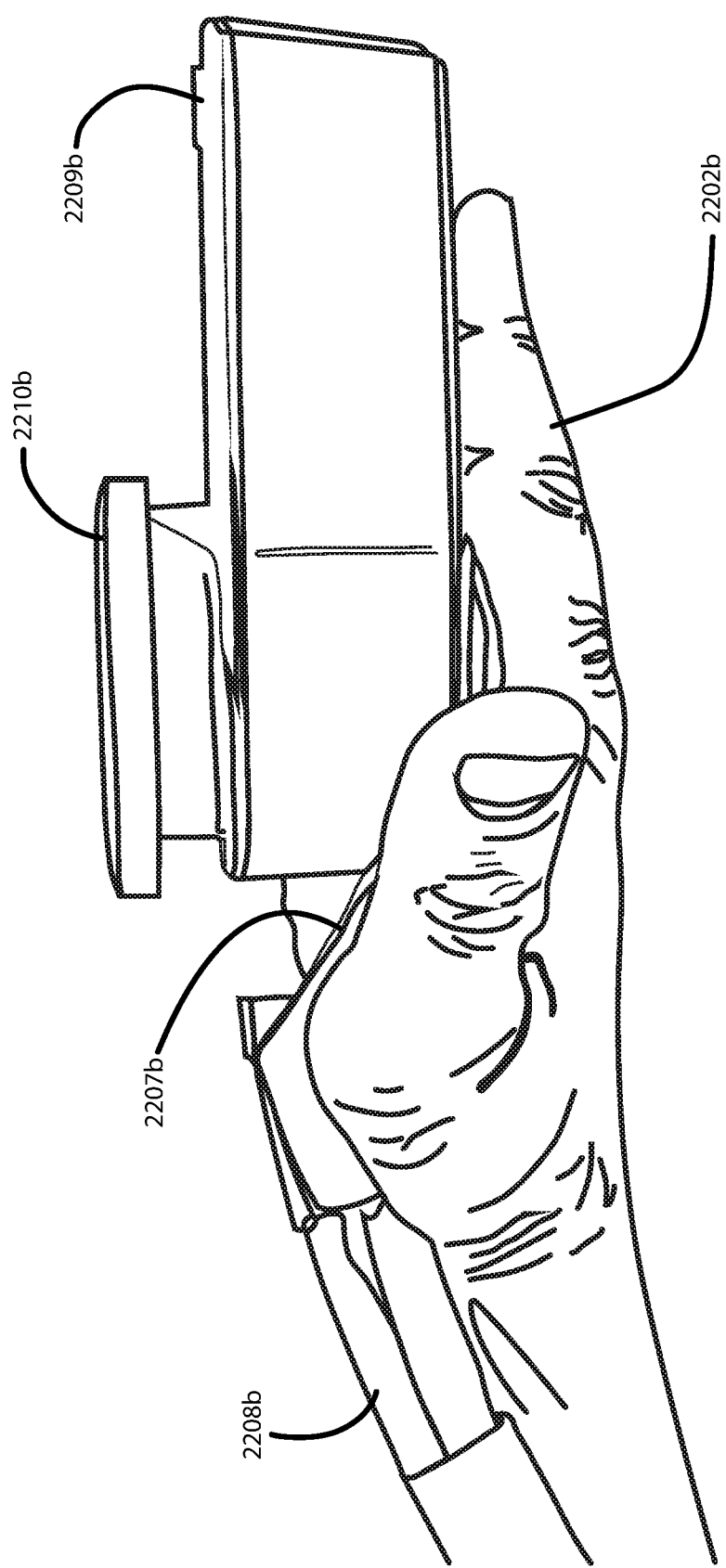
FIG. 23 illustrates a close-up view of the right-hand positioning during the control trial of the test method described in FIG. 22.

The recovery phase of the control trial consisted of seated rest for 18 minutes in a climate-controlled room at approximately 23° C. (73.4° F.) and 50% relative humidity. During the recovery phase the back of each hand rested on top of polyethylene bags 2206a and 2206b, filled with crushed ice. Additionally, the palms of the left hand 2202a and right hand 2202b were each cooled via direct contact with translucent fluid bladders 2207a and 2207b, through which water at an approximate temperature of 2° C. (35.6° F.) was continuously circulated, delivered via fluid transfer tubing sets 2208a and 2208b, connected to a fluid perfusion and thermal control device (Therma-Zone Continuous Thermal Therapy Device, Innovative Medical Equipment, Cleveland Ohio), not shown. Devices 2209a and 2209b, each with a light emitting diode array, were placed in direct contact with the translucent fluid bladders 2207a and 2207b, located on the palm of left hand 2202a and right hand 2202b. The light emitting diode arrays of devices 2209a and 2209b each provided monochromatic infrared energy with a central wavelength of 670 nm, a light intensity of 50 mw/cm$^2$, and a radiation area of 7.5 cm$^2$ (WARP 10A, supplied by Quantum Devices, Barneveld, Wis.). During the control trial, radiant infrared energy was pointed away from the hand and blocked from exiting the device via metal caps 2210a and 2210b, as also shown in FIG. 23. Thus no infrared energy entered into the hands during the control trial.

The exercise phase of the treatment trial consisted of elevated physical exertion, during which each subject rode a stationary cycle ergometer in a thermally-raised enclosure, just long enough for the subject to experience an elevation in core temperature of 0.5° C. (0.9° F.), approximately 3 to 5 minutes.

Figure 24:
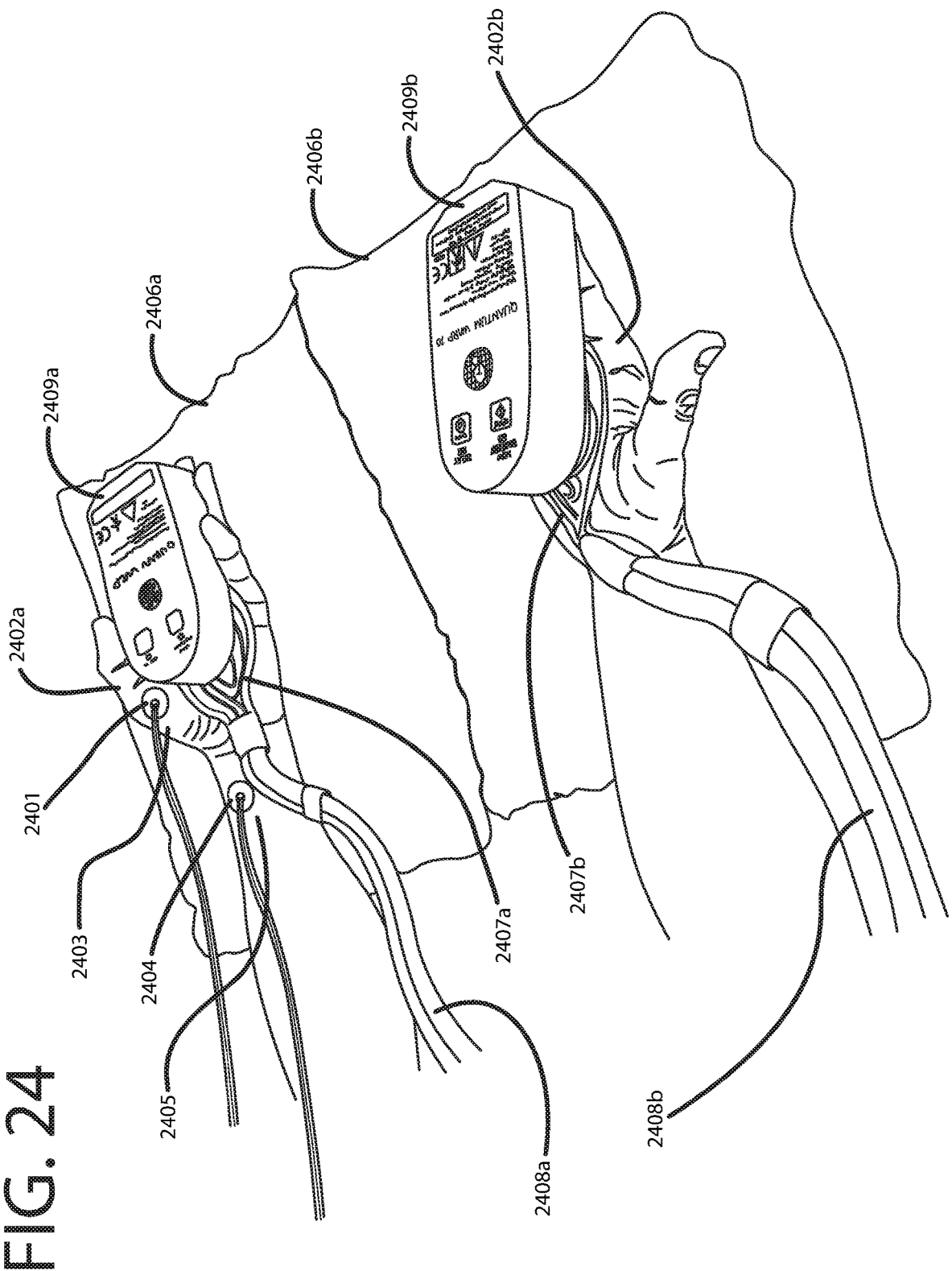
FIG. 24 illustrates the lower arm and hand positioning during the treatment trial of the second test method used to investigate the feasibility of the claimed method.

At the beginning of the recovery phase of the treatment trial, as shown in FIG. 24, one temperature sensor 2401 was placed on the palm side of the left hand 2402a, approximately located at the thenar eminence 2403. A second temperature sensor 2404 was placed on approximately the center of the left wrist 2405, palm side. Skin temperature at these locations was monitored during the recovery phase of the treatment trial.

Figure 25:
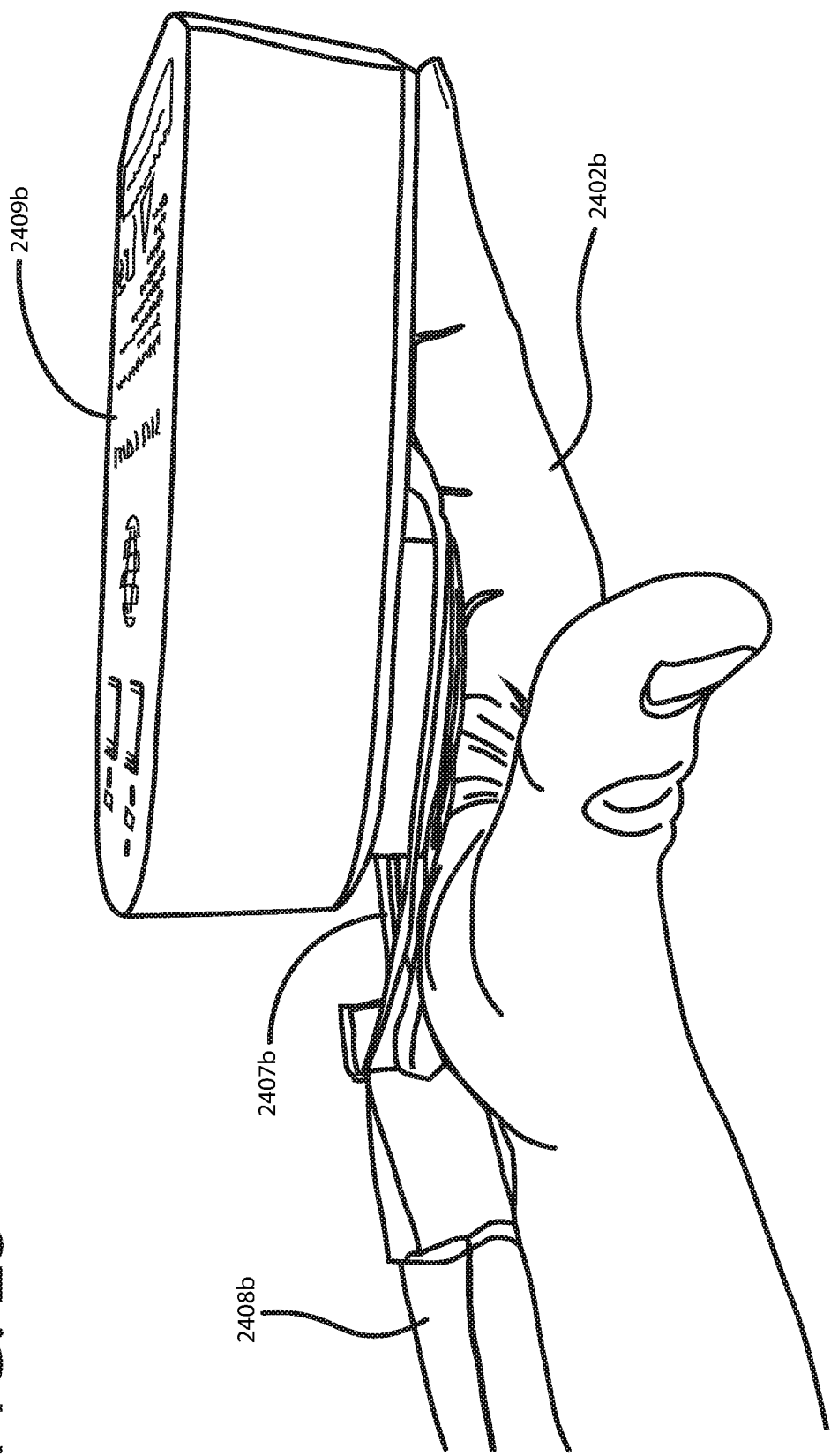
FIG. 25 illustrates a close-up view of the right-hand positioning during the treatment trial of the second test method described in FIG. 24.

The recovery phase of the treatment trial, consisting of seated rest for 18 minutes in a climate-controlled room at approximately 23° C. (73.4° F.) and 50% relative humidity, successfully utilized the claimed method to cool the core body temperature of two subjects. During the recovery phase the back of each hand rested on top of polyethylene bags 2406a and 2406b, filled with crushed ice. Additionally, the palms of the left hand 2402a and right hand 2402b were each cooled via direct contact with translucent fluid bladders 2407a and 2407b, through which water at an approximate temperature of 2° C. (35.6° F.) was continuously circulated, delivered via fluid transfer tubing sets 2408a and 2408b, connected to a fluid perfusion and thermal control device (Therma-Zone Continuous Thermal Therapy Device, Innovative Medical Equipment, Cleveland Ohio), not shown. Devices 2409a and 2409b, each with a light emitting diode array, were placed in direct contact with the translucent fluid bladders 2407a and 2407b, located on the palm of left hand 2402a and right hand 2402b. The light emitting diode array of devices 2409a and 2409b provided monochromatic infrared energy with a central wavelength of 670 nm, a light intensity of 50 mw/cm$^2$, and a radiation area of 7.5 cm$^2$ (WARP 10A, supplied by Quantum Devices, Barneveld, Wis.). During the treatment trial, the radiant infrared energy was directed through the translucent fluid bladders and into the palm of each hand, as also shown in FIG. 25.

Thus infrared radiant energy with a central wavelength of 670 nm bathed the palm of each hand during the recovery phase of the treatment trial but not during the recovery phase of the control trial. All other variables, including whole hand exposure to cold temperatures, were held constant between the control trial and the treatment trial.

Two of the three test subjects responded to the claimed cooling method, registering a significant difference in core temperature between the recovery phase of the control trial and the recovery phase of the treatment trial. Data in FIGS. 27-29 is representative of the two subjects that responded to the claimed cooling method.

Figure 27:
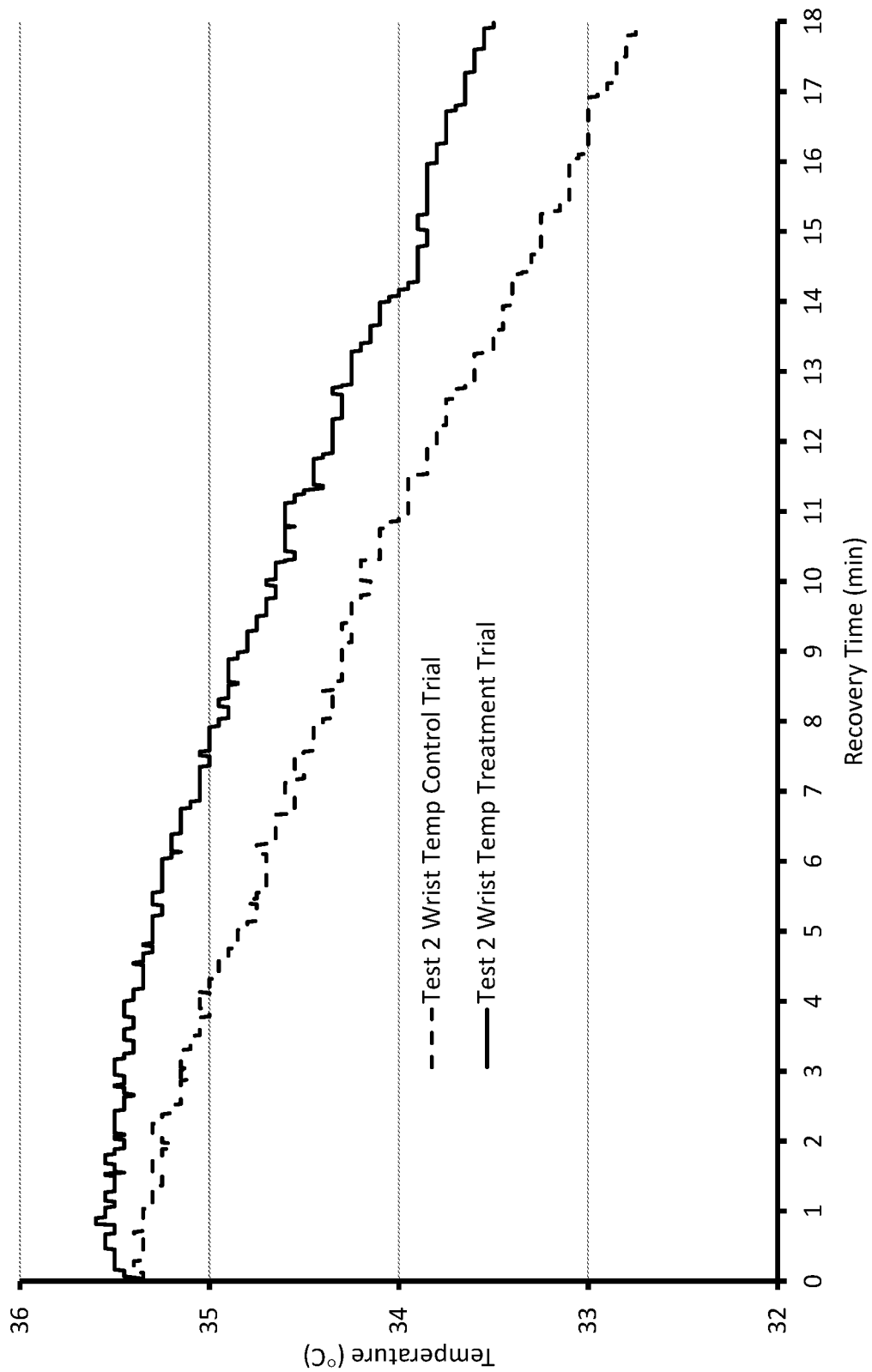
FIG. 27 illustrates the results as they pertain to wrist temperature of the control trial and treatment trial of the second test method described in FIG. 22.
Figure 28:
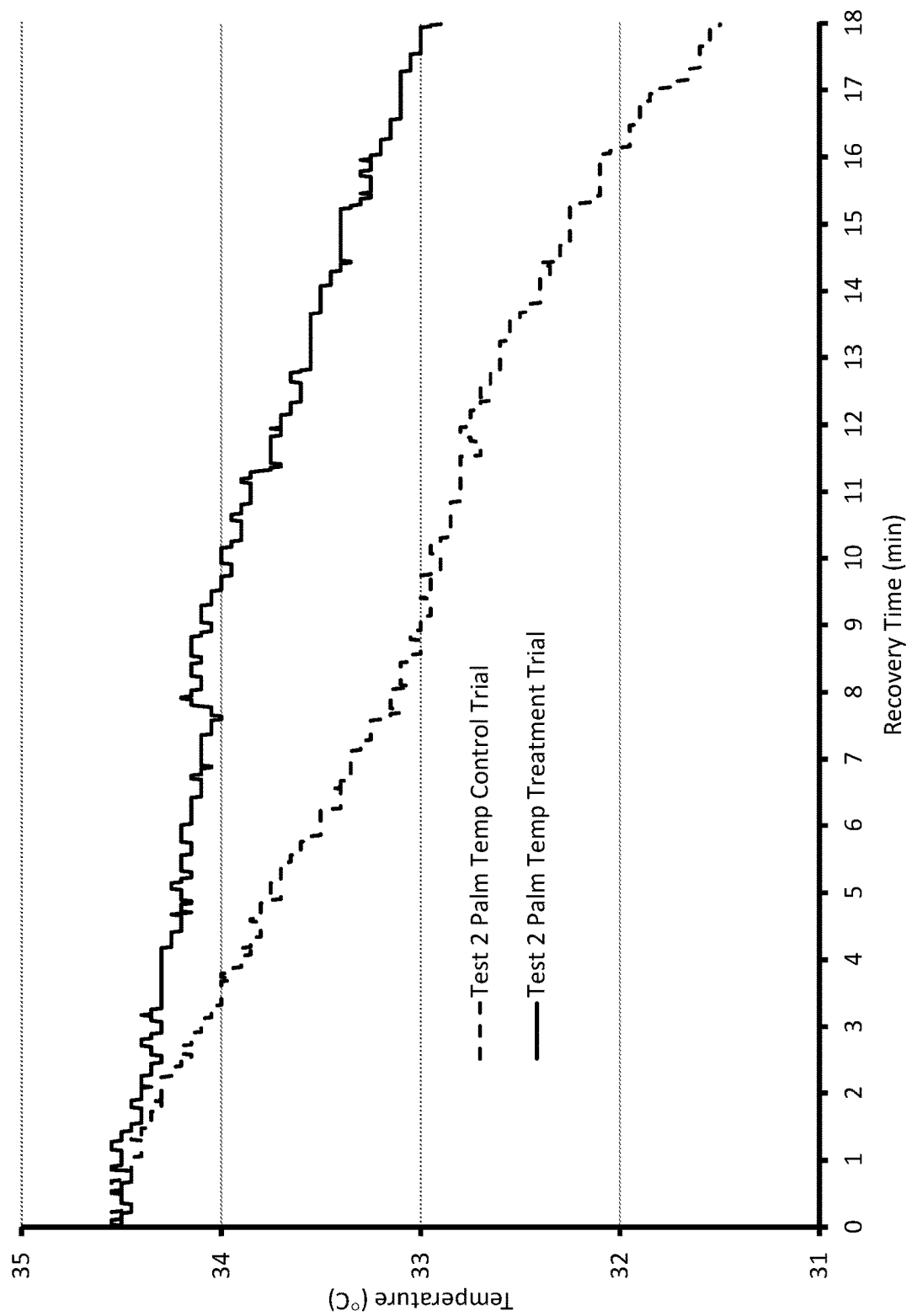
FIG. 28 illustrates the results as they pertain to palm temperature of the control trial and treatment trial of the test method described in FIG. 22.

Mean recorded skin temperatures at the wrist and palm of each subject were warmer during the recovery phase of the treatment trial compared to the recovery phase of the control trial, as demonstrated in FIG. 27 and FIG. 28, respectively. This data suggests that there was an increase in arteriovenous anastomosis vasodilation during the recovery phase of the treatment trial, compared to the recovery phase of the control trial.

Figure 29:
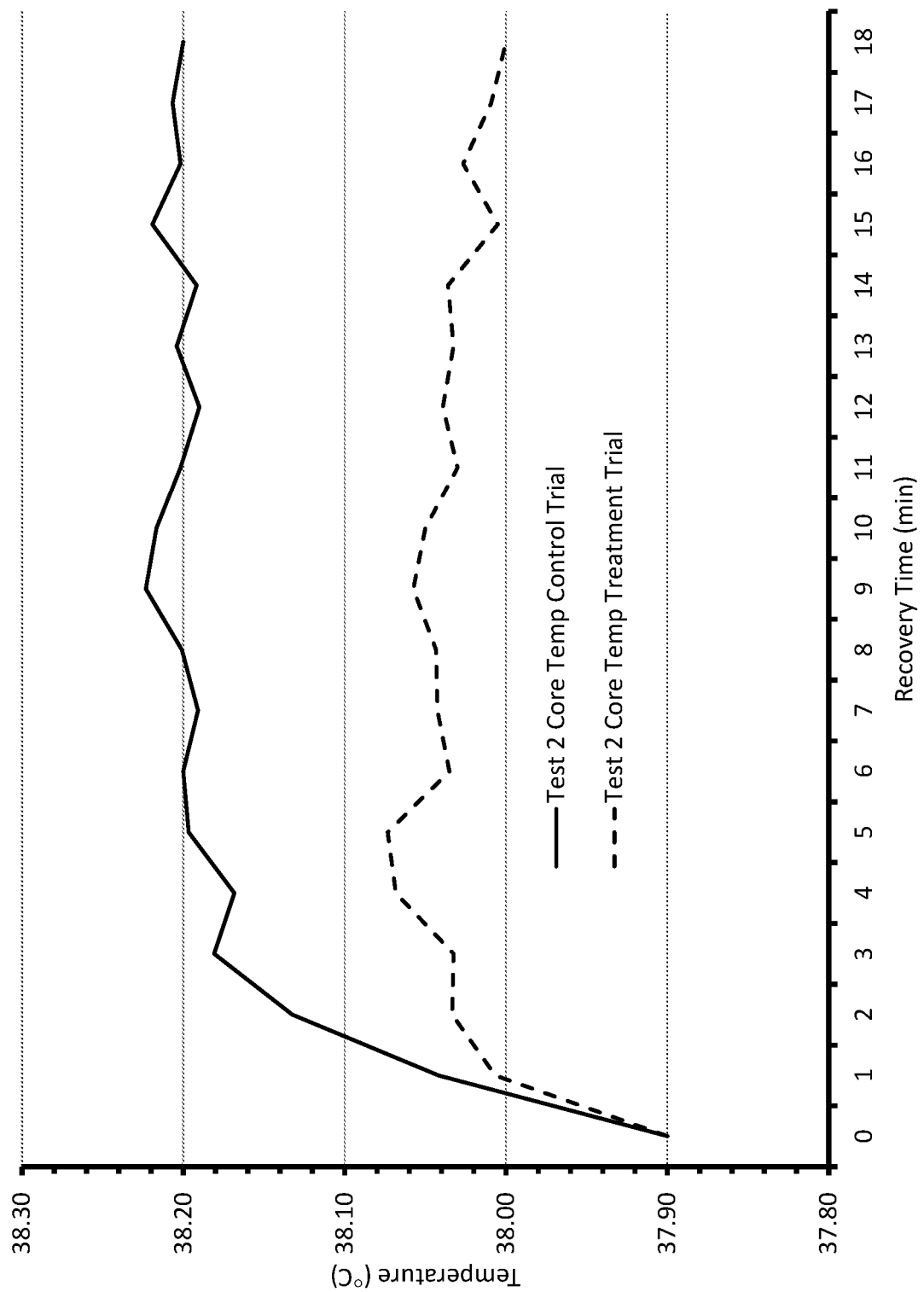
FIG. 29 illustrates the results as they pertain to core temperature of the control trial and treatment trial of the test method described in FIG. 22.

Mean core temperature data, as seen in FIG. 29, demonstrated a rapid rise of core temperature at the start of the recovery phase during both the control trial and the treatment trial. During the treatment trial, utilizing the cooling method of the present invention, the subjects experienced a relative difference in core temperature of −0.2° C. (−0.4° F.) compared to the control trial, by the end of the recovery phase.

It is anticipated and within the scope of the invention that the disclosed apparatus and methods can be used effectively in a variety of applications. The disclosed apparatus can be configured as a stationary system, a portable system, or a wearable system. It can be configured to transfer heat into the body, remove heat from the body, or both. It can be used to treat hypothermia and hyperthermia in a medical, ambulatory or home health environment.

It is anticipated and within the scope of the invention that when configured for heat removal from the body, the disclosed invention can be used for the following purposes: it can remove internal heat buildup during or immediately following physical exertion. As such it can be used to enhance physical performance of athletes. It could be incorporated into exercise equipment to enhance workout length, quality and capability. It can be used to increase stamina of soldiers or workers exposed to elevated temperatures. It can be utilized to prevent or reduce the effects of heat stress on any persons exposed to elevated temperatures, with or without physical exertion.

In a medical or home health environment, the invention can be used as the sole therapy or as an adjunct therapy for treatment of illnesses that affect the thermoregulatory system, such as fever, diabetes, high blood pressure or Parkinson's disease. Newborn and prematurely born children often have impaired thermoregulatory systems. In these cases the invention can be used to maintain normothermic core temperature, by adding or removing heat energy from the body as needed. A core temperature measurement and feedback control mechanism can be incorporated to form a closed loop system which maintains normothermic core temperatures of children or adults. One of ordinary skill in the art would recognize that this could also be applied to other mammals.

Deployed in a hospital environment and configured for transfer of heat into the body, the invention can be used to combat post-surgical hypothermia, which occurs in 60% of all surgeries and 90% of all cardiothoracic surgeries. It can be used to maintain normothermic core temperature during surgery by introducing heat into the body when a patient is located in a chilled surgical suite. This would allow for a cold surgical environment, which has proven to reduce the occurrence of life-threatening infections. A normothermic core body temperature during surgery also enhances the effectiveness of anesthesia agents, which allows for smaller doses required to be administered during surgery; additionally, a normothermic core temperature during surgery could eliminate post-surgical hypothermia, which would result in significantly reduced post-surgical recovery times. Alternatively configured for heat removal from the body, the invention could be used to induce surgical hypothermia, which is essential to enhance neuroprotection during certain high-risk surgical procedures.

Configured for transfer of heat into the body, the invention can be used to extend human exposure to cold environments, such as for workers exposed to the elements, or sports enthusiasts engaged in activities such as skiing, hiking, hunting, fishing, camping, climbing, snowmobiling, ocean swimming, etc. It can be used to rapidly heat the core temperature of people with severe hypothermia, which can cause significant bodily damage and loss of life. It can be used to assist in warm-up preparation prior to physical activities. It can be used in physical therapy to keep muscles and organs warm during extended cold therapy tissue treatments.

It is anticipated and within the scope of the invention that the invention could be used as an aid in weight loss by creating an extended, sustained removal of heat from the circulatory vasculature. This is because studies have shown that the sustained, moderate removal of heat from core organs, which puts a constant subthermal load on the body, must be countered through enhanced metabolic activity and thus the burning of calories.

Now that embodiments of the present invention have been shown and described in detail, various modifications and improvements thereon will become readily apparent to those skilled in the art. Accordingly, the exemplary embodiments of the invention, as set forth above, are intended to be illustrative, not limiting. The spirit and scope of the present invention is to be construed broadly.

The invention claimed is:

1. A device for modifying mammalian core temperature, comprising
   a first infrared energy source capable of emitting a first monochromatic infrared radiation with a central wavelength between 550 to 950 nm;
   a first translucent fluid bladder for thermal transfer;
   a first translucent substrate with a first surface in contact with the first translucent fluid bladder and a second surface configured to be in contact with a first open skin area of a mammal with a core temperature;
   a first fluid perfusion unit capable of circulating a first fluid through the first translucent fluid bladder, the first fluid set at a temperature above or below the core temperature of the mammal;
   wherein the first monochromatic infrared radiation from the first infrared energy source is capable of being directed through the first translucent fluid bladder and the first translucent substrate.

2. The device of claim 1 wherein the first translucent substrate is integral to the fluid bladder.

3. The device of claim 1 further comprising
   a second infrared energy source capable of emitting a second monochromatic infrared radiation with a central wavelength between 550 to 950 nm;
   a second translucent fluid bladder for thermal transfer;
   a second translucent substrate with a third surface in contact with the second translucent thermal fluid bladder and a fourth surface configured to be in contact with a second open skin area of the mammal with the core temperature;
   a second fluid perfusion unit capable of circulating a second fluid through the second translucent fluid bladder, the second fluid set at a temperature above or below the core temperature of the mammal;
   wherein the second monochromatic infrared radiation from the second infrared energy source is capable of being directed through the second translucent fluid bladder and the second translucent substrate.

4. The device of claim 3 wherein the first monochromatic infrared radiation and the second monochromatic infrared radiation are supplied by multiple light emitting diodes.

5. The device of claim 3 wherein the first monochromatic infrared radiation and the second monochromatic infrared radiation each has a central wavelength of 670 nm.

6. The device of claim 3 wherein the first monochromatic infrared radiation and the second monochromatic infrared radiation are supplied by a laser.

7. The device of claim 1 wherein the first translucent substrate is rigid and non-flexible.

8. The device of claim 1 wherein the first translucent substrate is flexible and configured to conform to the first open skin area of the mammal.

9. A method for regulating a core body temperature of a mammal through addition or removal of thermal energy, the method comprising:

monitoring the core body temperature of the mammal;

placing an open skin area of the mammal in contact with a first surface of a first translucent substrate;

directing a first infrared energy source emitting monochromatic infrared radiation energy with a central wavelength between 550 to 950 nm through a first translucent thermal transfer fluid bladder in contact with a second surface of the first translucent substrate and into the open skin area of the mammal; and circulating a first fluid, set at a temperature above or below the monitored core body temperature of the mammal, through a first fluid perfusion unit to raise or lower the core temperature of the mammal.

10. The method of claim 9 wherein the open skin area is located at a site where arteriovenous anastomoses blood vessels are beneath the surface of the skin.

11. A method for regulating a core body temperature of a mammal through addition or removal of thermal energy, the method comprising:

monitoring the core body temperature of the mammal;

placing an open skin area of the mammal in contact with a first surface of a first translucent substrate;

directing a first infrared energy source emitting monochromatic infrared radiation energy with a central wavelength between 550 to 950 nm through a second surface of the first translucent substrate and into the open skin area of the mammal; and setting the temperature of a heat pump located in contact with a second surface of the first translucent substrate at a temperature above or below the monitored core body temperature of the mammal, to raise or lower the core temperature of the mammal.

* * * * *